(12) United States Patent
Bucevschi et al.

(10) Patent No.: US 8,378,022 B2
(45) Date of Patent: Feb. 19, 2013

(54) BIOCOMPATIBLE, BIODEGRADABLE, WATER-ABSORBENT HYBRID MATERIAL

(75) Inventors: Mircea Dan Bucevschi, Rehovot (IL); Monica Colt, Rehovot (IL); Mendy Axlerad, Rehovot (IL)

(73) Assignee: Exotech Bio Solutions Ltd., Kiryat Gat (IL)

( * ) Notice: Subject to any disclaimer, the term of this patent is extended or adjusted under 35 U.S.C. 154(b) by 576 days.

(21) Appl. No.: 12/399,847

(22) Filed: Mar. 6, 2009

(65) Prior Publication Data
US 2009/0306290 A1 Dec. 10, 2009

Related U.S. Application Data

(63) Continuation of application No. 10/591,386, filed as application No. PCT/IL2005/000242 on Mar. 1, 2005, now abandoned.

(60) Provisional application No. 60/549,858, filed on Mar. 2, 2004.

(51) Int. Cl.
A61K 47/48 (2006.01)
(52) U.S. Cl. ............. 525/54.1; 524/17; 524/18; 524/47; 525/54.11; 525/54.4; 525/55; 525/63; 604/368; 604/372; 604/374
(58) Field of Classification Search .................... 524/17, 524/18, 47; 525/54.1, 54.11, 54.4, 55, 63; 606/368, 372, 374
See application file for complete search history.

(56) References Cited

U.S. PATENT DOCUMENTS

| | | | |
|---|---|---|---|
| 3,224,986 A | 12/1965 | Butler | |
| 3,926,869 A | 12/1975 | Horie et al. | |
| 3,926,891 A | 12/1975 | Gross et al. | |
| 3,935,099 A | 1/1976 | Weaver et al. | |
| 3,959,569 A | 5/1976 | Burkholder, Jr. et al. | |
| 3,980,663 A | 9/1976 | Gross | |
| 3,983,095 A | 9/1976 | Bashaw et al. | |
| 3,997,484 A | 12/1976 | Weaver et al. | |
| 4,076,663 A | 2/1978 | Masuda et al. | |
| 4,076,673 A | 2/1978 | Burkholder, Jr. | |
| 4,124,748 A | 11/1978 | Fujimoto et al. | |
| 4,190,562 A | 2/1980 | Westerman | |
| 4,264,493 A | 4/1981 | Battista | |
| 4,286,082 A | 8/1981 | Tsubakimoto et al. | |
| 4,349,470 A | 9/1982 | Battista | |
| 4,389,513 A | 6/1983 | Miyazaki | |
| 4,416,814 A | 11/1983 | Battista | |
| 4,459,068 A | 7/1984 | Erickson | |
| 4,525,527 A | 6/1985 | Takeda et al. | |
| 4,654,039 A | 3/1987 | Brandt et al. | |
| 4,666,983 A | 5/1987 | Tsubakimoto et al. | |
| 4,734,478 A | 3/1988 | Tsubakimoto et al. | |
| 4,883,864 A | 11/1989 | Scholz | |
| RE33,997 E | 7/1992 | Kuzma et al. | |
| 5,284,936 A | 2/1994 | Donachy et al. | |
| 5,292,802 A | 3/1994 | Rhee et al. | |
| 5,376,375 A | 12/1994 | Rhee et al. | |
| 5,385,983 A | 1/1995 | Graham | |
| 5,408,019 A | 4/1995 | Mertens et al. | |
| 5,447,727 A | 9/1995 | Graham | |
| 5,453,323 A | 9/1995 | Chambers et al. | |
| 5,487,895 A | 1/1996 | Dapper et al. | |
| 5,549,914 A | 8/1996 | Farber | |
| 5,565,519 A | 10/1996 | Rhee et al. | |
| 5,612,384 A | 3/1997 | Ross et al. | |
| 5,629,377 A | 5/1997 | Burgert et al. | |
| 5,712,316 A | 1/1998 | Dahmen et al. | |
| 5,733,576 A | 3/1998 | Chmelir | |
| 5,733,994 A | 3/1998 | Koepff et al. | |
| 5,736,595 A | 4/1998 | Gunther et al. | |
| 5,847,013 A | 12/1998 | Ross et al. | |
| 5,847,031 A | 12/1998 | Klimmek et al. | |
| 5,847,089 A | 12/1998 | Damodaran et al. | |
| 6,071,447 A | 6/2000 | Bootman et al. | |
| 6,107,432 A | 8/2000 | Engelhardt et al. | |
| 6,833,488 B2 | 12/2004 | Bucevschi et al. | |
| 2002/0193516 A1 | 12/2002 | Bucevschi et al. | |
| 2003/0215519 A1* | 11/2003 | Schwarz et al. | ............... 424/497 |

FOREIGN PATENT DOCUMENTS

| JP | 01 297484 A | 11/1989 |
|---|---|---|
| JP | 2000273446 | 10/2000 |

OTHER PUBLICATIONS

Kiatkamjornwong, Suda et al., Infulence of Reaction Parameters on Water Absorption of Neutralized Poly (acrylic acid-co-acrylamide) Synthesized by Inverse Suspension Polymerization,: J. Applied Polymer Sci., 72:1349-1366 (1999).

Amass, W et al., "A Review of Biodegradable Polymers: Uses, Current Developments in the Synthesis and Characterization of Biodegradable Polyesters, Blends of Biodegradable Polymers and Recent Advances in Biodegradation Studies," Polymers International, 47:89-144 (1998).

(Continued)

Primary Examiner — Robert Jones, Jr.
(74) Attorney, Agent, or Firm — Edgar W. Harlan; Carolyn S. Elmore, Esq.; Elmore Patent Law Group, P.C.

(57) ABSTRACT

A biocompatible, biodegradable, macromolecular water-absorbent hybrid material (WAHM), having a three-dimensional configuration with intermolecular covalent bonds and containing free functional groups, said polymer being formed by polymer-polymer intercoupling reaction between a natural water-soluble polymer A or its derivatives having a molecular weight between 20,000 and 300,000 Da, and a synthetic polymer B in an adequate ratio wherein the natural polymer A is selected from amphoteric reactants, partially denatured or chemically modified natural polymer, that dissociates in water to form both anions and cations, and which can undergo polymer-polymer intercoupling reactions, and wherein synthetic polymer B s a linear or branched reactive synthetic copolymer having a molecular weight of 50,000-500,000 Da derived from a vinyl monomer and an ethylenically unsaturated monomer, having a backbone with polymeric subunits covalently bonded to the polymer backbone, the subunits comprising ones with non-reactive and others with reactive chemical functional groups.

27 Claims, 4 Drawing Sheets

OTHER PUBLICATIONS

Chen, Jun et al., "Synthesis of superporous hydrogels: Hydrogels with fast swelling and superabsorent properties," J. Biomed. Mater. Res., 44(1):53-62 (Jan. 1999).

Choi, H.S. et al., "Volume Phase Transition Behavior of N-Isopropyl Acrylamide-N-Cyanomethyl Acrylamide Coolymer Gel Particles: The Effect of Crosslinking Density," J. of Applied Polymer Sci., 72:1091-1099 (1999).

Omidian, H. et al., Modified acrylic-based superabsorbant polymers (dependance on particles size and salinity) Polymer, 40: 1753-1761 (1999).

Schwarte, et al. "Novel poly (ethylene glycol)-grafted, cationic hydrogels: preparation, characterization and diffusive properties." Polymer, 39(24): 6507-6066 (1998).

International Search Report PCT/IL2005/000242, dated Jul. 8, 2005.

Bo, J., "Study on PVA Hydrogel Crosslinked by Epichlorohydrin", J. Appl. Polym. Sci., 46:783-786, 1992.

Fernandez-Nieves, A., et al., "Charge Controlled Swelling of Microgel Particles", Macromolecules, 33:2114-2118, 2000.

Foster, L.J.R., et al., "Activities of Extracellular and Intracellular Depolymerases of Polyhydroxyalkanoates", ACS Symposium Series 627, American Chemical Society, 1996.

Volke-Sepulveda, T., et al., "Microbial Degradation of Thermo-Oxidized Low-Density Polyethylene", J. Appl. Polym. Sci., 73:1435-1440, 1999.

Wool, R.P, et al., "Biodegradation Dynamics of Polymer-Starch Composites", J. Appl. Polym. Sci., 77:1643-1657, 2000.

Thakore, I.M., et al., "Morphology, Thermomechanical Properties, and Biodegradability of Low Density Polyethylene/Starch Blends", J. Appl. Polym. Sci., 74:2791-2802, 1999.

Okay, O., "Porous Maleic Anhydride-Styrene-Divinylbenzene Copolymer Beads", J. Appl. Polym. Sci., 34:307-317, 1987.

Nijenhuis, K., "Thermoreversible Networks-Viscoelastic Properties and Structure of Gels", Advances in Polymer Science, 130:1-12, 1997.

\* cited by examiner

BIOCOMPATIBLE, BIODEGRADABLE, WATER-ABSORBENT HYBRID MATERIAL

FIELD OF THE INVENTION

The present invention relates, generally, to composite materials that behave as hydrogels and to the methods for the preparation of such materials.

BACKGROUND

Materials that absorb water and aqueous media, including fluids secreted or eliminated by the human body are known. These materials are generally polymers based in the form of powders, granules, microparticles, films or fibers. Upon contact with aqueous liquid systems, they swell by absorbing the liquid phase in their structure, without dissolving it. When the swelling reaches equilibrium there is obtaining a gel, which frequently is called "hydrogel". If the water absorbency is more than 100 g water/g dried polymer the material is also called "superabsorbent" polymer.

Personal hygienic products (for example baby diapers, adult incontinence products, feminine hygiene products, and the like) are one of the highest consumers of hydrogels as superabsorbent polymers, in which the water- or aqueous media-absorbing material must have a high absorbance, both in free state and under pressure (with special reference to urine, menstrual fluid, human lactation or perspiration), to be biocompatible and to have the possibility to biodegrade. after use, by depositing the used products in landfill, which present biological activity (Bucholz F. L., Graham A. T., "Modern Superabsorbent Polymer Technology", John Wiley & Sons Inc. 1998).

The absorbency properties of hydrogels for manufacturing personal hygienic products have been achieved by well-known methods in art.

The free absorption and absorption under pressure, at the value accepted by the producers of the personal hygienic products, have been obtained with materials (singular or composite) based on ionic or non-ionic polymers and applying different methods of synthesis and then processing. The technical solutions, with known success of market, are offered by: a) poly(acrylic acid), copolymers of acrylic acid, partially neutralized, obtained by polymerization of mono- and polyfunctional monomers, different types of composite materials included (U.S. Pat. Nos. 3,926,891; 4,090,013; 4,117,184; 4,190,562; 4,654,039; 4,666,983; 4,808,637; 4,833,222; 5,118,719; 5,567,478; 5,629,377); b) starch cross-linked by graft polymerization with acrylonitrile, bifunctional monomers of polymerization, inclusively composite materials with the participation and other natural and/or synthetic polymers (U.S. Pat. Nos. 3,935,099; 3,997,484; 4,076,663; 5,453,323; 6,107,432) and respectively c) polyacrylamide, copolymers of acrylamide and composite materials using cross-linked polymerization starting from monomers or monomers and polymers (U.S. Pat. Nos. 4,525,527; 4,654,039; 5,408,019; 5,712,316). Other materials mentioned in prior of art, with potential success techno-economic uses: copolymers of maleic anhydride and polymeric composite (U.S. Pat. Nos. 3,959,569; 3,980,663; 3,963,095; 4,389,513; 4,610,678; 4,855,179), modified celluloses (U.S. Pat. Nos. 4,959,341; 5,736,595; 5,947,031; U.S. Pat. No.), poly(vinyl alcohol) and copolymers (U.S. Pat. No. 4,124,748), polyaspartates and copolymers (U.S. Pat. Nos. 5,284,936; 5,847,013).

For the other applied domains the requirements for the absorption under load correlated with the free absorption are much less strict, and for this reason are used a large variety of imacromolecular materials (Bo J., "Study on PVA Hydrogel Crosslinked by Epiclorohydrin", J. A. Fernandez-Nieves A., Fernandez-Barbero A., Vincent B., Nieves F. J., "Charge Controlled Swelling of Microgel Particles", Macromolecules, 33, 2114-2118, 2000, U.S. Pat. Nos. 4,264,493, 4,349,470; 4,416,814; 5,847,089; 3,224,986; 3,926,869; U.S. Pat. Nos. RE33,997, 5,487,895; 5,549,914; 5,565,519).

It is also known that materials which correspond from the point of view of absorption don't have the capacity of biodegradation in natural media (even in the case of composites based on biopolymers, because the degree of cross-linking conferred to satisfy the absorption under load, is too high compared to the thermodynamic conditions available for the biochemical reaction of degradation) and are not recommended for absorption of menstrual fluid or human lactation because contain different chemical combinations extractable by the aqueous media mentioned, which lead directly or indirectly to the appearance of rashes, inflammation or even toxic effects (because both inadequate chemical structure of some auxiliaries used and especially the technologies of synthesis and processing applied which can not permit an advanced purification which is efficient from the economical view).

Together with the increasing of interest for the "environmental protection" concept, appears a new vision in the strategy for the obtaining of polymeric materials for consumer goods, concretized by reconsidering the signification of biodegradability.

The terms "biodegradation" and "biodegradability" although used both at the level of scientifically communication and in mass media continue to generate much confusion. This situation is due especially of interpretation more or less correctly of the definition proposed for the respective terms. Accordingly with the terminological signification proposed by Poster I. R. J. and collaborators (Foster L. J. R., Fuller R. C., Lenz R. W.—in "Hydrogels and Biodegradable Polymers for Bioapplications", Ottenbrite R. M., Huang S. J., Park K. (Editors), ACS Symposium Series 627, American Chemical Society, Washington D.C., 1996), respectively Amass W. and collaborators (Amass W., Amass A., Tighe B.—*Polymer International* 47, 89, 1998) further, is presented a series of important aspects for present invention.

For purposes of this patent application, biodegradability is considered the property of a material the chemico-morphological structure of which is modified in a destructive manner (degradation), after interaction with media that contain microorganisms or biologically active combinations of substances generated by microorganisms, without participation or helped by none type of auxiliary with chemical degradation effect, which then favourize the biochemical process. The interaction mentioned represents a complex process called "biodegradation".

As any property and in the biodegradation case must be quantified, respectively to specify its values, with the purpose of systematization of the materials between itselves and to establish the ways of amplification or diminution. The biodegradation tests can be classified having in view the following criteria: 1) the factor's type with action of biodegradation: microorganisms; enzymes; 2) the type of medium which contain factor of biodegradation; environment: soil, water and air; living organisms: human and animal bodies; 3) the parameter used to evaluate the biodegradation: structural parameters (Volke-Sepulveda T., Favela-Torres E., Manzur-Guzman A., Limon-Gonzalez M., Trejo-Quintero G.—in *J. Appl. Polym. Sci.,* 73, (1999), 1435; Reeve M. S., McCarthy S. P., Downey M. J., Gross R. A.—in *Macromolecules,* 27, (1994), 825; Wool R. P., Raghavan D., Wagner G. C., Billieux S.—in J. Appl. Polym. Sci., 77, (2000), 1643; Thakore I. M., Iyer S., Desai A., Lele A., Devi S.—in *J. Appl. Polum. Sci.*, 74, (1999), 2791; Albertsson A. C., Barenstedt C., Karlsson S., Lindberg T.—in Polymer, 36, (1995), 3075), specific for spectroscopy (FTIR, NMR, RES etc.), electronic microscopy, DSC and others; biodegradability is quantified by coefficients that express the ratio between the value of structural indicators for initial material and the one who was biodegraded; phenomenological parameters (Spence K. E, Allen A. L., Wang S., Jane J.—in "Hydrogels and Biodegradable Polymers for Bioapplications". Ottenbrite R. M., Huang S. J., Park K. (Editors), ACS Symposium Series 627, American Chemical Society, Washington D.C. 1996), when the biodegradability is quantified by: weight loss, modification of the mechanical (rheological) properties' value, $O_2$ consumption, evolution of $CO_2$ emission; 4) the scale at which is made the biodegradation's experiment: laboratory (in vitro), effectuated with demonstrative purpose for a polymeric structure given, in principal with enzyme, with different specificities versus the support used, when the quantification is done both with structural parameters and phenomenological parameters (especially with by the weight loss and of the rheological properties' modification); it is used also the incubation in media with cells and/or microorganisms, respectively pilot scale.

The most controversial aspect of the biodegradation tests is referred at the manner in which these can offer information that correspond the criteria imposed by the environmental protection legislation. In this sense, it is considered that the biodegradation process can generate three different levels of structure's modification of a substance (Perrone C.—Poliplasti 398/399—january/february 1991, 66): a) primary biodegradation, characterized through that it is alter only a part from chemical structure, that means it is maintain the principal chain of the polymer and it is modified only some functional groups. In fact, the material maintain its volume, eventually the mass too but it can't be identified by specifically physico-chemical methods; b) partial biodegradation, characterized through that it is loosed the material integrity of substance, carried out by fragmentation of the volume in the same time with disappearance of an appreciable mass from the initial one. In facts from the material entity remain in the biological medium only secondary products, in gaseous, liquid or solid state (that can be in their turn pollutant factors); c) complete biodegradation, characterized through that the initial material entity disappears from biological medium as a result of the advanced fragmentation of molecules followed by the favoring of complete chemical degradation or/and their digestion by the microorganisms.

In accordance with what was mentioned above, in the prior of art there are known hydrogels, including superabsorbent polymers, which are purported to be biodegradable: (U.S. Pat. Nos. 4,944,734; 4,952,550; 4,959,341; 5,190,533; 5,417,997; 6,444,653), but in all cases the absorbency is inferior versus the traditional synthetic materials.

In our previous U.S. Patent Application, Pub. No: US 2002/0193516 A1, filed Mar. 30, 2001, is discussed about a biocompatible, biodegradable material water absorbent, with adequate absorbency, but which uses a method of synthesis and processing where is utilized organic solvents, that lead to high cost of production, because of the supplementary operation necessary for product purification and the technological effluents cleaning.

Biocompatibility is accepted to be a notion by whom is understanding a sum of biochemical characteristics which a material possess that make to be accepted by the living organisms (human, animals and plants), as an integral part of them, without resulting in spontaneous or in time the manifestation of a repulsive or toxic phenomenon in the form of inflammation, infections and others (Black J., "Biological Performance of Materials: Fundamentals of Biocompatibility", 2d ed. M. Dekker, N.Y., 1992).

The standards that have guided biocompatibility testing are the Tripartite Guidance; the International Organization for Standardization (ISO) 10993 standards, which are known as the Biological Evaluation of Medical Devices and remain under development internationally; and FDA blue book memorandum.

In accordance with the foregoing, a material is more biocompatible with a living organism the more similar the material to the organism's own biopolymers with which the material comes into contact. Thus, water- and aqueous media-absorbent materials presently known having advanced biocompatibility (even totally) intended to be in contact with human body are those that contain collagenic biopolymers: native collagen, solubilized collagen, gelatin and even collagen hydrolysate (Hoffman A. S., Daly C. H., "Biology of Collagen", Viidik Vunst J. Eds., Academic Press, New York, 1980; Ward A. G., Courts A., "The Science and Technology of Gelatin", Academic Press N.Y., 1977 and U.S. Pat. Nos. 5,376,375; 5,292,802; 5,945,101; 6,071,447 and others).

DESCRIPTION OF EMBODIMENTS OF THE INVENTION

In an embodiment of the present invention there is provided a hydrogel using a new type of composite material based on natural polymer and synthetic polymer.

In an embodiment of the present invention there is provided a water-absorbing hybrid material comprising amphoteric polymeric composite materials.

In an embodiment of the present invention there is provided a water-absorbing material, able to biodegrade in natural medium after its using in hygienic products.

In an embodiment of the present invention there is provided a superabsorbent material containing biopolymers that confer biocompatibility on contact with human body.

In an embodiment of the present invention there is provided a new type of macromolecular three-dimensional configuration by polymer-polymer intercoupling reactions between proteinaceous biopolymers and reactive synthetic polymers.

In an embodiment of the present invention there is provided a new type of superabsorbent polymer by using polymer-polymer intercoupling methods in which the reactive synthetic polymer has ionic reactive chemical groups.

In an embodiment of the present invention there is provided a process for preparing water-absorbing material which forms a three-dimensional network between functional groups that lead at covalent bonds without been accompanied of secondary products of reaction.

In an embodiment of the present invention there is provided a new method of synthesis and processing for the new water-absorbing material, based on a reaction mass as aqueous paste type, exclusively constituted from water and substances, partial or integral soluble in water, and having water as unique variable component in the material balance of the main flow sheet.

In an embodiment of the present invention there is provided the technology to obtain the new water and aqueous media absorbing material is integral ecological (non-pollutant raw materials and is not generated secondary products and neither pollutant waste) and lead to granular solids with reduced energy consumption.

DETAILED DESCRIPTION OF THE INVENTION

Figure 1:
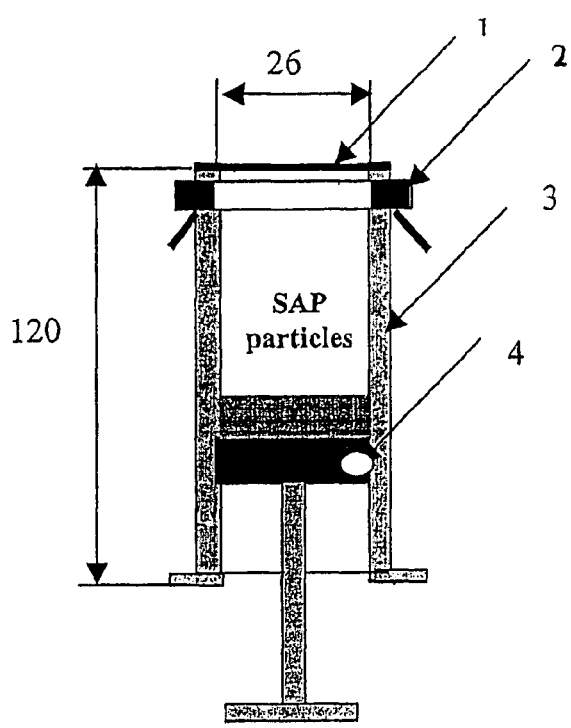
FIG. 1. Device of piston type for swelling and profiling used for rheological characterization of water-absorbing hybrid material (WAHM) hydrogels 1-polyester cloth of 100 mesh or PE foil; 2-ring of rubber; 3-cylinder of polyethylene; 4-the piston packing rubber FIG. 2. The variation of storage modulus G'[Pa] depending on radian speed (angular frequency) ω[rad/sec] for samples of reaction mass from Experiment 1 at different time intervals of polymer-polymer intercoupling.

In an embodiment of the present invention, the water-absorbing hybrid material (WAHM) is a composite material. In an embodiment of the invention the WAHM is biocompatible and/or biodegradable.

The term "composite material" used hereinafter, refers to a macromolecular product having a three-dimensional configuration, with intennolecular covalent and/or ionic and/or hydrogen bonds formed by polymer-polymer intercoupling reactions.

Optionally, the composite material also includes a one or more macromolecular products or other compounds providing special properties, such as biologically active compounds (i.e. drugs, stimulators, inhibitors, or anticoagulants, odorants, emollients, fertilizers, pesticides and others) when used in potential applications of the water-absorbing material.

In an embodiment of the present invention, the composite material is formed from two polymers, one designated "reactant A" and the other designated "reactant B".

Reactant A represents biopolymers. The structure of the biopolymers that enables to undergo polymer-polymer intercoupling reactions is the presence of certain free chemical functional groups, symbolized "u", that are: —OH; —SH; —$NH_2$ and —COOH.

In an embodiment of the present invention the biopolymers are proteins of animal or vegetable origin. In an embodiment of the present invention, reactant A is a biopolymer or derivatives thereof mentioned above which is soluble in water or aqueous solutions and has an average molecular weight not less than 20,000 Da and not more than 300,000 Da.

In an embodiment of the present invention reactant A is an "amphoteric reactant", i.e. it has chemical functions groups which dissociate in water to form both anions and cations and can undergo polymer-polymer intercoupling reactions. The presence of dissociable chemical functions groups does not exclude the optional presence of non-ionizable functional groups. In an embodiment of the present invention the biopolymers have primary amino functions, with a functionality "$f_{NH2}$" of at least $0.5.10^3$ moles $NH_2$/g and carboxylic functions, with a functionality "$f_{cooH}$" of at least $1.10^{-3}$ moles COOH/g, with isoelectric point (IEP) not less than 2.5 and not more than 10.5. In an embodiment of the present invention the amphoteric biopolymers are selected from: collagen, collagenic biopolymers (atelocollagen, solubilized collagen, gelatin and collagen hydrolysate) obtained from terrestrial and marine resources and derivatives of those, -alfa-keratose, gama-keratose, keratin hydrolysate and derivatives, elastin and derivatives, fibrin and derivatives, fibroin and derivatives, ovalbumine, bovine serumalbumine and albumine derivatives, casein and its derivatives, soybean protein and its derivatives.

The term "protein derivatives" refers to proteins chemically modified by acylation reactions. The acylation may be effected using known methods.

In an embodiment of the present invention the modifying agent is a carbonylic compound. Useful modifying agents include anhydrides and acid chlorides. Examples of anhydrides are phthalic anhydride; maleic anhydride; citraconic anhydride; itaconic anhydride; succinic anhydride. Examples of acid chlorides are: benzoyl chloride, benzenesulfonyl chloride and butyrylchloride.

In an embodiment of the present invention, the chemical functions' content that belong to modifying agent and that are found on protein derivatives are not less than $1.10^{-5}$ moles/g and not more than $1.10^{-2}$ moles/g, for example between $1.10^{-4}$ moles/g and $1.10^{-3}$ moles/g.

In an embodiment of the present invention the biopolymers are proteinaceous j biopolymers and their derivatives accepted by pharmaceutical industry and which are commercially available, such as: collagen and collagenic biopolymers (gelatin, collagen hydrolysates), keratin hydrolysates, fibrin, casein or soybean protein. In an embodiment of the present invention the biopolymer is gelatin (food grade or pharmaceutical grade), obtained from specific resources (hides, tendons and other types of conjunctive tissues).

In an embodiment of the present invention the reactant B, which leads to forming the polymeric composite material after the polymer-polymer intercoupling with "reactant A" is a synthetic polymer. In an embodiment of the present invention it is a reactive linear or branched synthetic copolymer, obtained either via single stage chemical processing, such as polymerization, polycondensation, etc. In an embodiment of the present invention it is obtained via a two stage polyreaction process, followed by chemical modification (known as "polymer-analogous transformations").

In an embodiment of the present invention the reactivity of reactant B enabling it to undergo polymer-polymer intercoupling is due to certain types of functional groups, one of which is a reactive chemical function, symbolized by "r", in comparison with free chemical functions of the biopolymers as well as a non-reactive chemical function, symbolized by "n", which generally do not react with covalent bonds.

In an embodiment of the present invention the reactive synthetic copolymers have an average molecular weight not less than 10,000 Da and not more than 500,000 Da. In an embodiment of the present invention the reactive synthetic copolymers have reactive chemical functions in the form of reactive substituents, symbolized as "R-r", and no n-reactive substituents, symbolized as "R-n", where:

R is a chemical group attached by one or more covalent bonds to the atoms of the backbone or the branches of the backbone of the synthetic polymers. R may itself In an embodiment of the present invention there is provided a reactive or non-reactive chemical function, and may contain another group, known as a "spacer", which is interposed between the chemical function and the chain that is anchored to this one. An example of chemical structures of spacers are —CO—O— and —$(CH_2)_n$— with n equal from 1 to 4.

In an embodiment of the present invention polymers with groups that intervene in the chemical process by ionic mechanism are used. For example, the reactive chemical functions may be unaccompanied by secondary products, with the occasion of a covalent bond's forming. For another example, ionogen reactive chemical functional groups are represented by —CO—O—CO— and —CO—NH—CO—, such as:

maleic anhydride, citraconic anhydride, citraconic anhydride, 2-octenylsuccinic anhydride and respectively, the adequate imides. In an embodiment of the present invention the anyhydride is maleic anhydnide or itaconic anhydride.

In the context of the present patent application, it is accepted that the non-reactive substituents on the reactant B belong to at least "m" number of different structural types. In an embodiment of the present invention, with m=1; 2; 3 or 4. In an embodiment of the present invention m=1 or 2. Examples of non-reactive substituents are: hydrogen, aliphatic or aromatic hydrocarbonate residues with 1 to 20 carbon atoms, non-activated esteric groups, etheric, iminic or non-activated halogenated derivatives. Optionally, under specific reaction conditions of polymer-polymer intercoupling, the non-reactive substituent may be represented by atomic groups, as such, or only part of these, that represent polar chemical functions, for instance hydroxyl, amino, amido or carboxylic groups.

In accordance with an embodiment of the present invention, non-reactive substituents are attached to the backbone of the copolymer, that represent monomer residues. In an embodiment of the present invention the monomers, carrying the non-reactive substituents are selected from: styrene, alpha—methylstyrene, alkylated styrenes such as ethylstyrene or tert-butylstyrene, vinyl-toluene, vinyl esters of saturated $C_1$-$C_4$-carboxylic acids such as vinyl formate, vinyl acetate or vinyl propionate, alkyl vinyl ethers with at least 2 carbon atoms in the alkyl group, such as ethyl vinyl ether or butyl vinyl ether, acrylate or methacrylate esters such as 2-ethylhexyl acrylate, n-butyl acrylate, isobutyl acrylate, t-butyl acrylate, hexyl acrylate, n-butyl methacrylate, lauryl methacrylate and isodecyl methacrylate; conjugated diolefins such as butadiene, isoprene, and piperylene; allenes such as allene, methyl allene and chloroallene; olefin halides such as vinyl chloride, vinyl fluoride and polyfluoro-olefins, ethylene, propene, isobutylene, butadiene isoprene, esters of monoethylenically unsaturated $C_3$-$C_6$-carboxylic acids, i.e. esters of monohydric $C_1$-$C_8$-alcohols and acrylic acid, methacrylic acid or maleic acid, monoesters of maleic acid, i.e. monomethyl maleate, and hydroxyalkyl esters of said monoethylenically unsaturated carboxylic acids, i.e. 2-hydroxyethyl acrylate, hydroxypropyl acrylate, hydroxybutyl acrylate, hydroxyethyl methacrylate, hydroxypropyl methacrylate and hydroxybutyl methacrylate, N-vinyllactams such as N-vinylpyrrolidone or N-vinylcaprolactam, acrylic and methacrylic esters of alkoxylated monohydric saturated alcohols, vinyl pyridine and vinyl morpholine, N-vinylformamide, dialkyldiallylammonium halides such as dimethyldiallylammonium chloride, diethyldiallylammonium chloride, allylpiperidinium bromide, N-vinylimidazoles such as N-vinylimidazole, 1-vinyl-2-methylimidazole and N-vinylimidazolines such as N-vinylimidazoline, 1-vinyl-2-methylimidazoline, 1-vinyl-2-ethyliimidazoline or 1-vinyl-2-propylimidazoline, acrylamide, methacrylamide or acrylonitrile.

In an embodiment of the present invention the monomers are selected from ethylene, propene, styrene, isobutylene, vinyl acetate, methyl acrylate, methyl methacrylate, acrylamide, vinylether, N-vinylpyrrolidone, acrylic acid, methacrylic acid and maleic acid.

Optionally, the non-reactive substituent may be a reactive chemical function which is consumed before the polymer-polymer intercoupling reaction is completed by a "special combination", using known methods of coupling.

In an embodiment of the present invention the functionality of reactant B, in accordance with ionogen reactive chemical functions, symbolized by "$f_r^B$", is not less than 5.104 moles "r"/g and not more than $1.10^{-2}$ moles "r"/g.

In an embodiment of the present invention the reactive synthetic polymers are accepted by the pharmaceutical industry and are commercially available. For example, among the ionogen reactive chemical function are: poly (ethylene-alt-maleic anhydride), poly(ethylene-graft-maleic anhydride), poly(isobutylene-co-maleic anhydride), poly(isoprene-graft-maleic anhydride), poly(maleic anhydride-co-1-octadecene), poly(propylene-graft-maleic anhydride), poly(styrene-co-maleic anhydride), etc.

The term "polymer-polymer intercoupling", refers to the chemical process of forming covalent bonds which occur between a number of polymers with different macromolecular structure, through chemical functions that every polymer possesses and without the intervention of any micromolecular substance, such as a crosslinking agent or coupling agent.

A polymer-polymer intercoupling reaction is exemplified schematically in Scheme 1 for a system formed from two reactants, polymer A and polymer B.

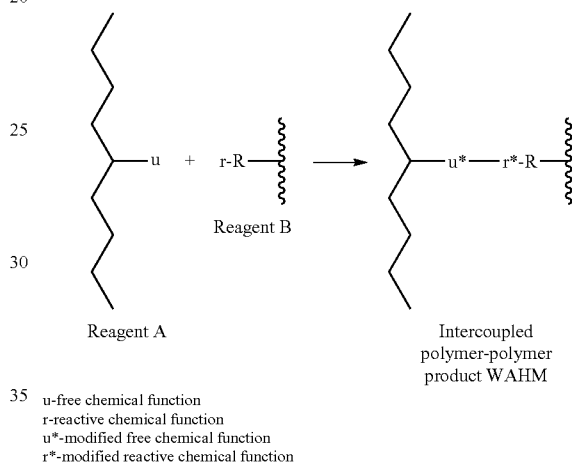

Scheme 1

Reagent A + Reagent B → Intercoupled polymer-polymer product WAHM u-free chemical function
r-reactive chemical function
u*-modified free chemical function
r*-modified reactive chemical function Intercoupling reactions between different types of polymers A and B having various reactive chemical functions, representing embodiments of the present invention, are shown schematically in Scheme 2.

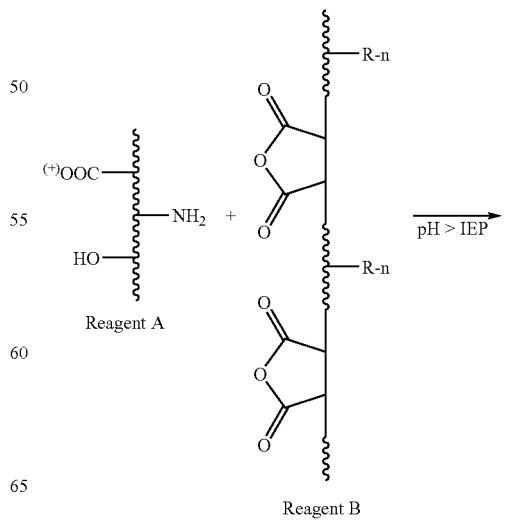

Scheme 2

Reagent A + Reagent B → (pH > IEP)

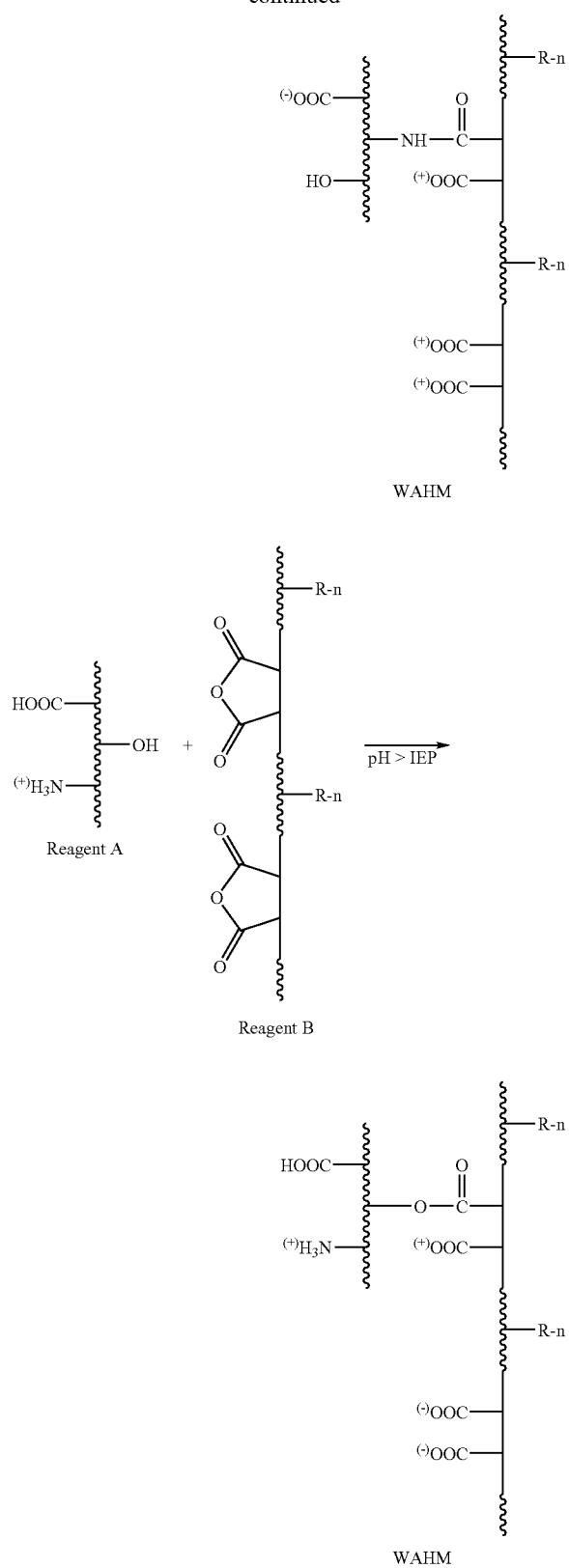

In an embodiment of the present invention, polymer-polymer intercoupling between reactant A and reactant B occurs by a chemical process in water.

ILLUSTRATIVE AND NON-LIMITATIVE EXAMPLES OF THE INVENTION

The Preparation of Water Absorbent Hybrid Material (WAHM) by Chemical Process in Water The term "chemical process in water" refers to the fact that the synthesis of three-dimensional structure of water absorbent hybrid material occurs in water, by using reactants as solutions or suspensions, for their preparing has been exclusively used water.

In an embodiment of the invention, a chemical process in water of polymer-polymer intercoupling includes three stages:
1) preparation of aqueous reactants, called: reactant 1 (R1); reactant 2 (R2) and reactant 3 (R3);
2) polymer-polymer intercoupling by mixture of the reactants R1, R2 and R3
3) reaction mass processing for obtaining water absorbent hybrid material.

1) Aqueous Reactants Preparation
a) Reactant R1

A suitable amount of solid biopolymer (reactant A), may be dissolved in a volume of water with a conductivity less than 10 μS and a temperature of 60° C., by mixing the two components in adequate ratios to obtain solutions with concentration not less than 1% and not more than 20%, preferably between 2% and 10%. This solution with concentration and temperature specified being represented as R1.

b) Reactant R2

A quantity of solid reactive polymer B, as powder or granules, may be suspended in water with conductivity less than 10 μS, by mixing the two components in adequate ratio to obtain a solid-liquid dispersion with a concentration in solid not less than 5% and not more than 35%, for example between 15% and 25%. This aqueous dispersion is called "water dispersion WD-1".

The water dispersion of reactive polymer B, WD-1, is stirred for 0.5 hours at a room temperature. In the end, the solid phase is separated by filtration at vacuum. The wet solid is washed for 3 times with a quantity of water, which represents a mass of 3 to 5 times higher than the initial quantity of reactive polymer B used for its preparation. It is obtained a wet solid symbolized by "WS".

This solid WS is introduced into a blender to which is added a quantity of water, to obtain a new solid-liquid aqueous dispersion with a concentration of solid of not less than 20% and not more than 50%, for example between 30% and 40%. This aqueous dispersion is called "water dispersion WD-2".

The water dispersion WD-2 is mixed at room temperature for not less than 5 minutes and not more than 25 minutes, for example between 10 and 20 minutes, at a speed not less than 1000 rpm and not more than 5000 rpm, preferably between 2500 rpm and 3500 rpm. The resultant aqueous dispersion, is represented as R2.

c) Reactant R3

A suitable amount of base is dissolved in a volume of water with conductivity less than 10 μS, by mixing the two components in adequate ratios to obtain solutions with concentration not less than 5% and not more than 35%, for example between 10 and 20%. The resulting solution represents reactant R3.

The base may be, for example, lithium hydroxide, sodium hydroxide, potassium hydroxide, ammonium hydroxide, lithium carbonate, lithium bicarbonate, sodium carbonate, sodium bicarbonate, potassium carbonate, potassium bicarbonate and ammonium bicarbonate. They can be used individually or as a mixture.

2) Polymer—Polymer Intercoupling

In a dual-shaft jacketed kneader reactor, with a speed ratio between stirrer and shaft $n_1$: $n_2$ not less than 1:1.05 and not more than 1:1.4, for example between 1:1.1 and 1:1.2, with a slow speed of rotor (1) not less than 20 rpm and not more than 250 rpm, for example between 60 rpm and 120 rpm, equipped with a heating-cooling jacket and thermometer, are introduced first the reactant R2 and then under mixture is added the whole quantity of reactant R1 in adequate ratio so to represent not less than 0.1% and not more than 99% from the mixture in dry state formed from polymer A and polymer B, for example between 5% and 35%. The mixture of reactant R1 and reactant R2 is mixed not less than 10 minutes and not more than 40 minutes, preferably between 15 minutes and 25 minutes, at a temperature not less than 15° C. and not more than 75° C., for example between 35° C. and 55° C. Then is added the whole quantity of reactant R3 in adequate ratio not less than 1% and not more than 25%, for example between 5% and 20% of dried base based on dried mixture of polymer A and polymer B. The mixing continues not less than 1 hour and not more than 12 hours, for example between 3 hours and 8 hours, at temperature of reaction mass before the reactant R3 was added.

When the mixing is stopped the reaction mass has an aspect of a granular transparent hydrogel and is very elastic.

3. Reaction Mass Processing

The reaction mass obtained in the kneader is profiling with screw extruder, having the same constructive characteristics with device called "meat chopper", as a bundle of rods with 40 . . . 100 mm in diameter. The hydrogel rods are laid on metallic framework covered with screen from polyester with mesh of 250 microns. The frameworks are introduced in a circulating warm air oven for drying the hydrogel by evaporation. The water evaporation occurs in warm-air current at a temperature not less than 40° C. and not more than 100° C., for example between 50° C. and 90° C. and a speed of air circulation of 0.5-1.5 m/s. The water evaporation process (drying) is ended when the solid mass as rods type achieve a humidity content not less than 3% and not more than 15%, for example between 7% and 12%.

The mass of rods that comes out of oven is ground in a mill with cones, adjusted to obtain granules with equivalent diameter of particles included between 150 microns and 2500 microns. The granular mass is then cooled at ambient temperature, collected in polyethylene bags and is deposited in conditioning rooms with air circulation at temperature of 25±5° C. and relative humidity of 55±10% for a period of time not less than 24 hours and not more than 96 hours, for example between 48 hours and 72 hours.

Finally, the conditioned granular mass, representing water absorbent hybrid material (WAHM), is packed in polyethylene bags, that after their filling are closed by sealing.

Samples of WAHM were tested in accordance with the procedure outlined, which follows.

Methods of Analysis and Testing

1. Percent Moisture (U.S. Pat. No. 5,629,377)

The percent moisture values reported herein are defined as the percent weight loss of a 10 g sample of ground resin in a circulating air oven at 105° C. over 3 hours. Additional weight loss during pre-treatment was measured by difference.

2. Particle Size 2

ASTM D1921-89: Particle size (Sieve Analysis) of Plastic Materials

3. Free Absorbency Capacity (FAC)

To determine the FAC, 0.2±0.0005 g of absorbent product (WAHM) (particle fraction 125-800.mu.m) are weighed into a tea bag measuring 60×60 mm, which is then welded. The material weight is called "$W_s$". Then is weighted the tea-bag with the solid sample and the weight is called "$W_d$". The tea bag is then introduced into a beaker that contain 250 grams aqueous medium with temperature of 37° C. The beaker is introduced in a thermostatic water bath (JULABO-Eco Temp TW8) where is maintained the same temperature. After 60 minutes of swelling, the tea bag is removed from the aqueous medium; hang up axially the tea-bag for 15 minutes in order to drain the excess water media and then is weighed at analytical balance. The weighted mass is called "$W_w$".

In parallel, an empty tea-bag is weighed at analytical balance and the weight obtained is called "$W_E$". Then is introduced in aqueous medium with temperature of 37° C., where it is maintained for 60 minutes. In the end the tea-bag is removed from medium; hang up axially the tea-bag for 15 minutes in order to drain the excess water media and then is weighed at analytical balance, obtaining the weight "$W_A$". It has been effectuated 5 samples with empty tea-bags, and is calculated the average weight of aqueous medium kept by tea bag and is called "$W_t$", with relation:

$$W_t = \tfrac{1}{5}\Sigma(W_A - W_E)$$

Free absorbency capacity of sample, $(FAC)_s$, is calculated with relation:

$$(FAC)_s = (W_w - W_d - W_t)/Ws, [g/g]$$

It has been done three tests in similar conditions that was mentioned above and the free absorbency capacity of the absorbent material, $FAC_{WAHM}$, is evaluated as average of resulted obtained from the three tests, with relation:

$$FAC_{WAHM} = \tfrac{1}{3}\Sigma[(FAC)_s], [g/g]$$

As aqueous medium has been choiced:
water with a conductivity of 4.3 μS, resulted FAC in water;
tap water
aqueous solution of NaCl of concentration 0.9%, resulted FAC in salt solution,
aqueous dispersion obtained by mixing 3 dose of baby's milk powder, commercial product SIMILAC, resulted FAC in baby milk.

4. Absorbency Under Load, (AUL)

The test is effectuated with a plastic sample cup. The sample cup consist of a plastic cylinder having 1 inch inside diameter and an outside diameter of 1.25 inch. On the end of sample cup is applied an 100 mesh polyester cloth, which was fixed on the tube's wall with a cable ties, that it immobilized very good the plastic screen (which was very well stretch).

To carry out the test, 0.16±0.0001 grams ($W_{s,aul}$) sample of the WAHM (for baby milk is used samples with only 0.1±0.0005 grams), which has been sieved to particle size between 250 and 710 microns, is placed into the sample cup and spread uniformly as a layer on the polyester screen of the sample cup. The sample is then covered with a plastic spacer disc, weighing 4.4 grams, which is slightly smaller than the inside diameter of the sample cup, and serves to protect the sample from being disturbed during the test. A weight of 20; 100; 200 or 300 grams is then placed on the spacer disc, thereby applying a load of about 0.06; 0.3; 0.6 and respectively 0.9 pound per square inch. The sample cup with WAHM sample and weight is weighed ($W_{d,aul}$) The sample cup is placed in a Petri dish, with diameter of 60 mm, that contain 70-80 grams of medium with temperature of 37° C., and which is immersed in a thermostatic water bath (JULABO-Eco Temp TW8) at the same temperature, to begin the test. After 60 minutes the sample cup containing the swollen WAHM with the weight still placed on the plastic spacer disc is removed from aqueous media. Any excess aqueous media on the polyester screen of the sample cup is removed by gently blotting with a paper towel (the weight should still be in the sample cup during blotting). This blotting continue by moving the sample cup to a new area of the dry paper towel until no visible water mark is made on the towel. Then the sample cup containing swollen WAHM and weight is weighed ($W_{w,aul}$).

Also has been done three tests with plastic sample cup without WAHM, in the same conditions that was used for test with absorbent material, obtaining the average weight of aqueous medium retain by polyester screen called $W_{p,aul}$, which has been calculated with relation $$W_{p,aul} = \frac{1}{3}\Sigma(W_{A,aul} - W_{E,aul})$$

Absorbency Linder load of sample, $(AUL-X)_s$, is calculated with relation:

$$(AUL-X)_s = (W_{w,aul} - W_{d,aul} - W_{p,aul})/W_{s,aul}, [g/g]$$

where X=0.06 or 0.3 or 0.6 or 0.9, values that represent the pressure at which occurred the swelling.

It has been done three tests in similar conditions that was mentioned above and absorbency under load of the absorbent material, $AUL_{WAHM}$-X, is evaluated as average of resulted obtained from the three tests, with relation:

$$AUL_{WAHM}\text{-}X = \frac{1}{3}\Sigma[(AUL-X)_s], [g/g]$$

The aqueous media used has been the same with those was mentioned at free absorbency capacity analysis.

5. Centrifuge Retention Capacity, (CRC)

To determine the CRC, the tea-bag with the sample of material that was swelled in salt solution (FAC in salt solution) is centrifuged at 250 g for 3 minutes. The amount of liquid retained by the WAHM is determined by weighing the centrifuged tea bag ($W_c$), and CRC is calculated with relation:

$$CRC_{WAHM} = \frac{1}{3}\Sigma[((W_w - W_d - W_t) - W_c)/W_3)_s], [g/g]$$

6. Rheological Tests a) The Kinetic of Polymer-Polymer Intercoupling Reaction

To demonstrate that chemical process of polymer-polymer intercoupling occurs in the mixture constituted from R1, R2 and R3 and progresses in time has been extracted samples from reaction mass that was analyzed by rheological test of Oscillation Frequency Sweep type. The testing has been done with Controlled Stress Rheometer, Rheo Stress 1, from Thermo HAAKE-Germany), equipped with Cylinder Sensor System Z20 DIN which comprise one rotor and one beaker, in accordance with the standard DIN 53019/ISO 3219. The test has been done at 25° C., with following setting: $\omega$=0.6283–628.3 rad/s; $\Sigma$=0.01 Pa; gap=4.2 mm.

The experimental data obtained have been processed graphically, as dependence G' (storage modulus) versus $\omega$, with a software Fheo Win Pro, from the same company.

b) Gel Rigidity Determination

For the evaluation of hydrogels' mechanical properties, obtained after the swelling of solid WAHM sample in a solution of 0.9% NaCl, has been used the rheological parameter "Gel Rigidity" (Rodol A. B., Cooper-White I., Dunstan D. E., Boger D. V.—Polymer, 42, 2001, 185-198]) defined by relations:

$$E = \lim_{\omega \to 0} G'(\omega)$$

$$G'(\omega) = E + K\omega^n$$

where:
E=gel rigidity, [kPa]
G'($\omega$)=storage modulus, [kPa]
$\omega$=oscillation frequency, rad/s
k,n=material constants.

The gel rigidity, E, has been evaluated from the rheological experiments of Oscillation Frequency Sweep type, with the rheometer RheoStress 1 from ThermoHaake company with a plate-plate sensor system PP35.

0.5±0.001 g of WAHM particles with the particles' dimension in 250÷710 μm domain are introduced in a device of piston type presented in the FIG. 1.

Over the mass of WAHM particles is pouring 10 mL of 0.9% NaCl solution with 37° C. and the upper part of cylinder (3) is covered with a foil of polyethylene (1) that is fixed with the rubber ring (2), with the purpose to avoid the drying of the hydrogel by water evaporation.

After 60 minutes of WAHM particles' contact with saline solution, the polyethylene foil is changed with a polyester cloth of 100 mesh and is fixed on cylinder with the rubber ring (2). Then, is moving the piston (4) till the layer of hydrogel formed is in contact with polyester cloth (1). Further, the device of piston type is rotated in vertical plane with 180° and is putted in a glass funnel with the purposes to drain the excess of the swelling liquid (saline solution) from the hydrogel layer. After that, is putted on the superior part of the piston (4) a weight of 200 g with purposes to filling the free volume which was remained in the space of cylinder between the nylon cloth and piston with the hydrogel mass and in the same time to realize a reduced draining of the liquid hold back between the swelling particles.

After 15 minutes from the applying of the weight, when isn't seen a drain of liquid from hydrogel, the weight is removed, the device of piston type is taken out from the funnel, and the rubber ring (2) and the nylon cloth (1) are removed.

Then is pressed on the piston (4) till is evacuated from the device a cylinder of hydrogel with the thickness of 3 mm. With a knife is sectioned the cylinder of profiled hydrogel and resulted a disc with thickness of 3 mm, which is putted in the middle of the fix plate of the sensor component of plate—plate type from Rheometer.

After the positioning of the hydrogel disc, is moved the mobile plate of the sensor over the sample till the distance between the two plates is 1.5 mm. Finally, is beginning the rheological stress.

All the experiments have been done in the frequency domain $\omega$=062831±628.3 rad/s, at the 25° C. temperature (room temperature).

The experimental data have been processed with the software Rheo WinPro from ThermoHaake company. Three specific values are evaluated at a testing of Oscillation Frequency Sweep type. The experimental points corresponding to the G' curve, have been fitted in connection with the rheological model. After the fitting, is obtained the value for gel rigidity, GR, [kPa].

7. Biodegradation Capacity (Relative Gel Rigidity after 48 Hours of Interaction with Pepsin)

For the evaluation of the biodegradability capacity of the WAHM sample has been applied a method based on rheological evaluation.

"Rheological Evaluation" meant to evaluate the intensity of biodegradation process that puts in evidence the variation of Gel Rigidity of WAHM hydrogel versus the interaction time with a proteolytic enzyme's solution and the result expressed as Relative Gel Rigidity (RGR), [%], versus the value of the same rheological parameter corresponding to the material which has not suffered an enzymatic attack.

The testing of biodegradability capacity of WAHM samples is done based on experimental indication found in U.S. Pat. No. 5,733,994 using the enzymatic preparation PEPSIN (from porcine gastric mucosa) with 0.7 FIP-U/mg for biochemistry, EC 3.4.23.1-MERCK, catalog no. 107185.

To determine the relative gel rigidity (RGR), in two series of 5 tubes with screw cap each of them that has a capacity of 5 mL, are introduced in each one 0.3±0.0005 g of granular material of WARM, with particles dimension between 250 and 710 µm and 20 mL PEPSIN solution (dissolved in solution of 0.1% HCl in distilled water) of concentration 2% (weight percentage). The first series of 5 tubes called "blank series" has been putted in refrigerator at 4° C. The second series called "biodegradation test series" has been putted at incubation at 37° C. in a thermostatic water bath JULABO model EcoTemp EW8.

Further, from each series has been taken a tube at the following period of time: 15 minutes; 2 hours; 24 hours, 48 hours or 1 week. In each tube is introduced 2 mL solution of $NH_4OH$ of concentration 1N, and the system is let at the temperature room during 30 minutes. The gel mass formed is separated from the excess of the liquid by free filtration through filter paper (Double Rings Filter Paper-202 Ashless, XINHUA PAPER MILL, Cat no. 1202110) and is putted to the determination of Gel Rigidity with the rheometer Rheo-Stress 1 (ThermoHaake) using Cylinder Sensor System Z20DIN.

Gel Rigidity for each hydrogel sample has been evaluated by experiments of Oscillation Frequency Sweep type that has been described above.

Relative Gel Rigidity (RGR) has been evaluated with relation:

$$RGR^{(h)}, [\%] = \frac{E_{(37° C.)}^{(h)}}{E_{(4° C.)}^{(h)}} \times 100$$

where:

$E_{(37° C.)}^{(h)}$·Gel Rigidity, [kPa] of the sample with Pepsin at temperature of 37° C., that belonging to "biodegradation test series"

$E_{(4° C.)}^{(h)}$·Gel Rigidity, [kPa] of the sample with Pepsin at temperature of 4° C., that belonging to "blank series"

(h)—time of maintaining of sample at the specified temperature, [hours]

8. Polymer Moisture Tension 0.2 g of SAPs' particles have been putted in a tea bag (used for determination of Free Absorbency) for free swelling and the assemble weighted at analytical balance is immersed in 500 ml liquid (of different water types) for 2 hours. Then the bag is removed from the swelling liquid and is hang up axially to drain the excess liquid. After 15 minutes the bag with hydrogel is weighted and is calculated the free absorbency that was expressed in g/g.

After that in a filter funnel of 100 ml capacity (interior diameter 52 mm and 73 mm height) with a filtering medium from sintered glass with a porosity of 2 (pores with dimension between 40 . . . 100 µm—catalog Brand) and tare made at analytical balance, are introduced 30 g gel (measured at analytical balance). Then the funnel filter that contains gel is putted in an Buchner filter flask for filtering under vacuum, connected at vacuum pump of Rotovac device, equipped with automated system of vacuum's control and digital view. Then is selected the value of suction and is putted on the vacuum pump. After 10 minutes of vacuum's action, the system is returned at atmospheric pressure and the funnel filter is weighted at analytical balance. Is recorded the weight loss that is expressed in the end as free absorbency g/g.

Then the funnel is fixed again at the suction installation which was fixed at a higher value of vacuum that is maintain again for a period of 10 minutes, after this is repeated the operations mentioned above.

With the same quantity of hydrogel has been done suctions at 940; 900; 850; 800; 750 and 700 mbar. The results have been expressed graphically as dependency Absorbency=f (suction)

EXAMPLE 1

In a 5 liter beaker, equipped with stirring rod of anchor type with two blades is prepared 2.8 kg solution of reactant A, by dissolving 280 g of gelatin type A, 175 Bloom, from swine (Aldrich, catalog no. 27, 161-6), with Mv=85,000 (estimated according to the method from Veis A.—"The Macromolecular Chemistry of Gelatin", Academic Press, New York, 1964), $f_{NN2}=0.65 \cdot 10^{-3}$ moles/g and $f_{COOH}=1.32 \cdot 10^{-3}$ moles/g (values estimated according to Ward A. C., Courtis A.—"The Science and Technology of Gelatin", Academic Press, New York 1977) in 2.52 kg water with temperature of 35° C. and conductivity of 4.3 µS. The solution had a concentration of 10%, represents the reactant R1.

In a reaction vessel of 10 titer, equipped with a stirring rod of anchor type with four blades, thermostatic jacket and thermometer are introduced 7 liter water with a conductivity of 4.3 µS and 1.4 kg SCPIPSET 520 (poly(styrene-co-maleic anhydride)) with an average molecular mass of 350,000 Da from Hercules Incorporated as reactant B, with a functionality in anhydride groups $f_r^B=0.00286$ moles of maleic anhydride per 1 g polymer, evaluated by the method which is based on reaction of anhydride groups with morpholine and titration of morpholine in excess with perchloric acid in acetic acid (Okay O., "Porous Maleic Anhydride-Styrene-Divinylbenzene Copolymer Beads", *J. Appl. Plym. Sci.*, 34, 307-317, 1987). Aqueous dispersion of reactive polymer B, WD-1 is stirred 0.5 hours at room temperature and the solid phase is separated by filtration at vacuum. The wet solid is washed of 3 times with 2 liter water each time. It is obtained 3.2 kg wet solid (WS) of polymer B. Further, is introduced in a blender of 5 liter, WS of polymer B and 1.3 kg water. The aqueous dispersion WD-2 is mixed at room temperature for 15 minutes, at a speed of 3500 rpm. Is resulted 4 kg aqueous dispersion, which contain 31% solid phase of reactive polymer B, represents the reactive R2.

In a 5 liter beaker, equipped with stirring rod of anchor type with two blades is prepared 2.8 kg solution of base, by dissolving 280 g NaOH in 2.52 kg water with a conductivity of 4.3 µS. The resulted solution of concentration 10%, represents the reactant R3.

In a dual-shaft jacketed kneader reactor of 20 liter, with a speed ratio between stirrer and shaft $n_1:n_2$ of 1:1.2, with a slow speed of rotor (1) not less than 60 rpm, equipped with a heating-cooling jacket and thermometer are introduced first 4 kg reactant R2 and then with mixing is added the whole quantity of 2.8 kg reactant R1. The mixture of reactant R1 and reactant R2 is mixed for 15 minutes, at temperature of 35° C. After homogenization is pulled out 20 grams of mixture (sample called "S-0") for rheological characterization, in conformity with method Rheological tests from chapter "Methods of Analysis and Testing".

Then is added 2.8 kg reactant R3. The mixing continues for 3 hours at 35° C. During intercoupling reaction has been extracted 5 samples of 20 grams each at time intervals of: 15 min; 30 min; 60 min; 120 min and 180 min (the samples have been called "S-15"; "S-30"; "S-60"; S-120" and "S-180").

Figure 2:
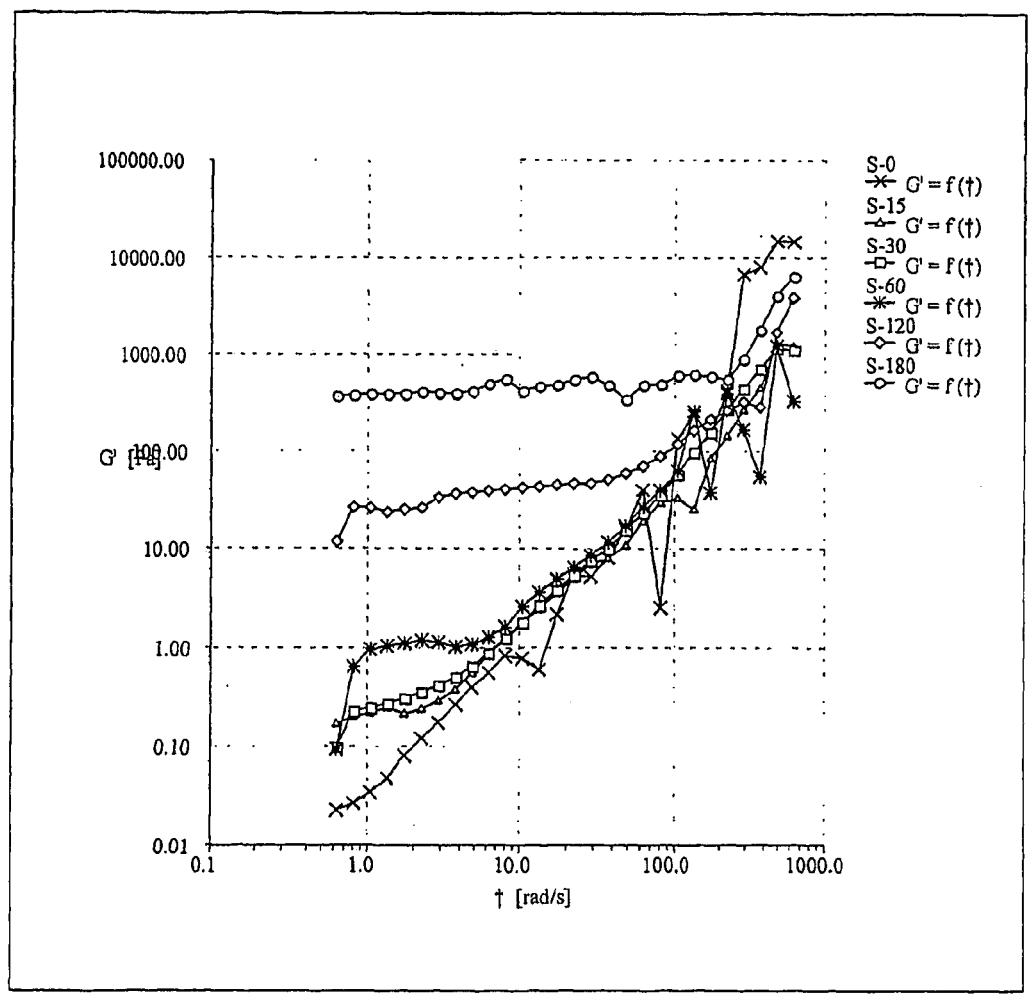

The variation mode for storage modulus of reaction mass versus angular speed and reaction time presented in FIG. 2 illustrates the mixture transformation from an entity material of fluid type (suspensions, corresponding to samples S-0; S-15 and S-30) in a material of gel type (S-60; S-120 and S-180). The gel state is established gradually after 60 minutes and is accentuated after 2 hours of intercoupling reaction (Nijenhuis K., "Thermoreversible Networks-Viscoelastic Properties and Structure of Gels", *Advances in Polymer Science*, 130, 1-252, 1997).

After evacuation of reaction mass from kneader, is obtained 9.32 kg of transparent granular hydrogel, very elastic.

Further, the hydrogel mass is profiling with screw extrude, having the same constructive characteristics with device called "meat chopper", as a bundle of rods with 40 . . . 50 mm in diameter. About 1.5 kg of rods from the quantity of hydrogel was lay on metallic framework covered with screen from polyester with mesh of 100 microns (6 frameworks). These 6 frameworks are introduced in laboratory air circulation oven (Model UT12 HERAEUS from Kendro Laboratory Products Germany) for drying by water evaporation from wet material. The water evaporation occurred in warm-air current at 85° C., at a speed of air circulation of I m/s for 2.5 hours, controlling from 30 in 30 minutes the humidity content from material, by gravimetrical method, with Moisture analyzer (Model SMO 01 from BOECO GERMANY).

After drying and cooling at room temperature is obtained 2.08 kg of solid material with humidity content of 8.51%. Further, this is grinded with a microfine grinder drive (Model MF 10.2 from IKA-WERKE GMBH & CO. Germany). Is obtained 1.986 kg of granular material with particles' dimension bigger than 125 microns and smaller than 800 microns and 0.094 kg of powder with particles' dimension less than 125 microns (the grading analysis has been done with Vibratory Sieve Shaker "Analysette 3" equipped with a control and evaluation programme "AUTOSIEVE for Windows" from FRITSCH GMBH Germany).

Further, the granular mass with particles bigger than 125 microns is collected in polyethylene bags and is deposited in conditioning room with air circulation at temperature of 25±5° C. and relative humidity of 65%, for 48 hours.

Finally, is obtained 1.96 kg water absorbent hybrid material (WAHM-1) from which 1.8 kg is packed in polyethylene bags, that after their filling are closed by sealing, and the rest of 0.16 kg WAHM-1 has been putted to the tests that are described in the chapter "Methods of Analysis and Testing".

The results of the tests effectuated are presented in table 1.

TABLE 1

Properties WAHM -1 from example 1.

| Properties | Unit | Average Values (from 3 samples) |
|---|---|---|
| Appearance | | White-Yellow Particles |
| Humidity content | % | 11.05 |
| Free Absorbency in water | G/g | 146 |
| Free Absorbency in salt solution | G/g | 48.6 |
| AUL in salt solution with Areal Polymer Distribution (APD) 0.2 [g/in$^2$] | | |
| AUL at 0.3 psi | G/g | 23.8 |
| AUL at 0.6 psi | G/g | 19.1 |
| AUL at 0.9 psi | G/g | 16.8 |
| Free Absorbency in baby milk | G/g | 26.5 |
| AUL in baby milk with Areal Polymer Distribution (APD) 0.1 [g/in$^2$] at 0.1 psi | G/g | 19.7 |

TABLE 1-continued

Properties WAHM -1 from example 1.

| Properties | Unit | Average Values (from 3 samples) |
|---|---|---|
| Centrifuge Retention Capacity (CRC) In salt solution | G/g | 23.5 |
| pH 1 g in 100 ml salt solution | | 7.13 |
| Gel Rigidity, in salt solution | KPa | 2.33 |
| Relative Gel Rigidity Decreasing after 48 hours (Biodegradation Capacity) | % | 62.23 |

Figure 3:
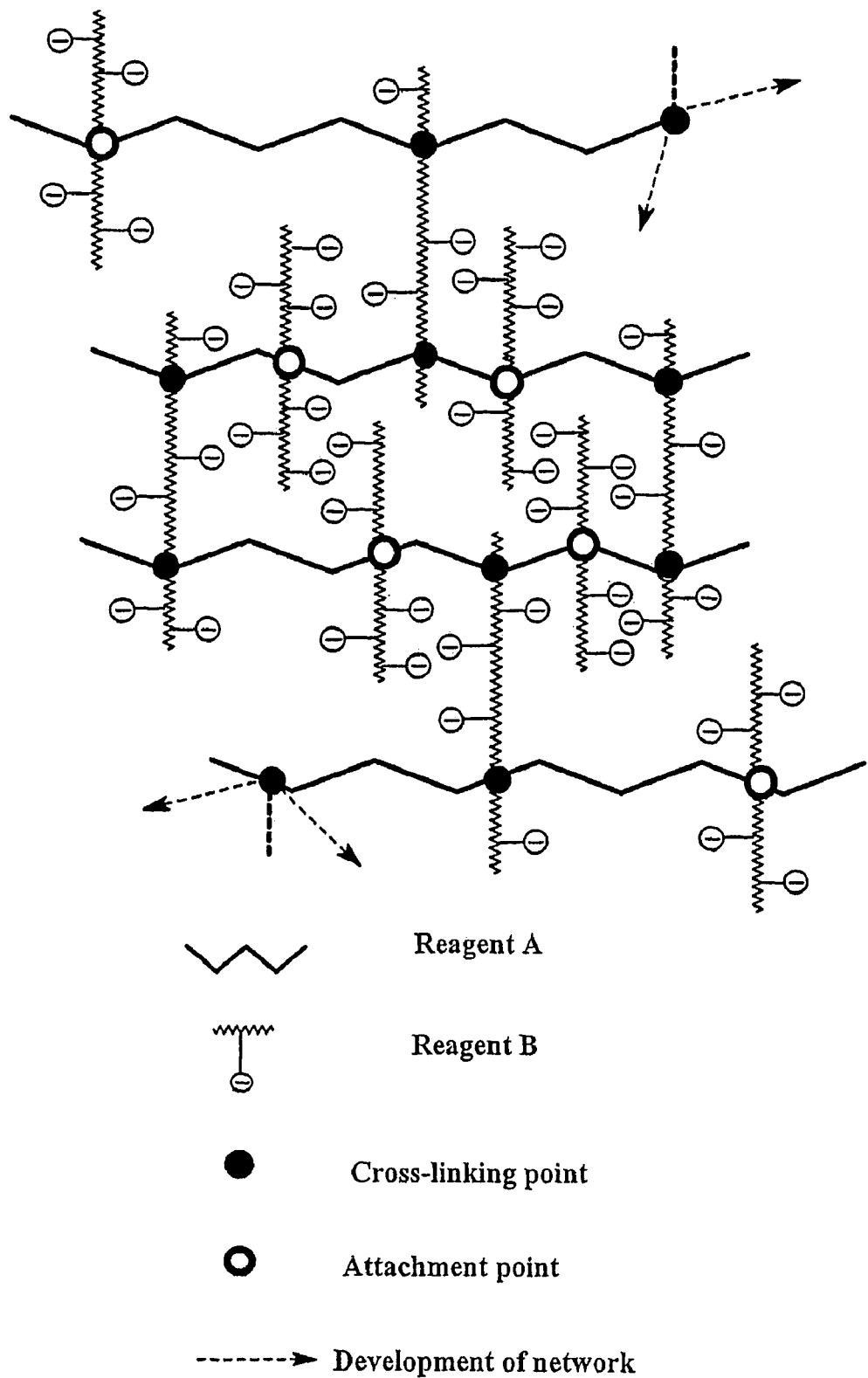
FIG. 3. Model of three-dimensional structure of polymer-polymer intercoupling reaction product between reactant A and reactant B.

The properties of new water absorbing hybrid material (WAHM) are resulted from specific structure of the three-dimensional polymeric composite network, which is presented in FIG. 3. The fragments from chains of polymer A and polymer B covalent bonded of cycle rank in attachment points, interacting in interior of "network eye" generating repulsive force (thermodynamic incompatibility). These lead at an interaction parameter Floty-Huggins "$\Psi_{AB}$" of opposite sign versus polymer-solvent parameter "$\chi_{AW}$" and "$\chi_{BW}$", that induce the increasing of contribution of mixing at global value of swelling osmotic pressure (Klempner D., Frisch K. C.—"Advances in Interpenetrating Polymer Networks", vol. I, Technomic. Publ. Co. Inc. Lancaster, SUA, 1990)

EXAMPLE 2

The same method of preparing and the same equipment as in Example 1 with the difference that: the reactant R1 is represented by 2 kg solution of gelatin type A, 300 Bloom, from swine (Aldrich, catalog no. 27, 160-8), with concentration of 20%; reactant R3 is represented by 2.1 kg KOH solution. It is obtained 2.14 log water absorbing hybrid material (WAHM-2).

EXAMPLE 3

The same method of preparing and the same equipment as in Example 1 with the difference that at the intercoupling reaction occurs at 55° C. for 3 hours. It is obtained 1.93 kg water absorbing hybrid material (WAHM-3).

EXAMPLE 4

The same method of preparing and the same equipment as in Example 1 with the difference that: the reactant R1 is represented by 2.2 kg solution of gelatin type B, 225 Bloom from calf skin (Aldrich, catalog no. 27, 162-4) with concentration of 30%; the reactant R2 is prepared using poly(styrene-alt-maleic anhydride) with Mn=50,000 (ACROS catalog no. 17925-2500); the reactant R3 is represented by 1.5 kg LiOH solution with concentration of 15%; the drying of reaction mass is done at 50° C., for 5 hours, when is obtained a solid material with humidity content of 7.63%. It is obtained 2.07 kg water absorbing hybrid material (WAHM-4)

The absorbency in salt solutions and capacity of biodegradation of water absorbing hybrid materials obtained in experiments 2-4 are presented in table 2.

TABLE 2

The properties for WAHM-2; WAHM-3 and WAHM-4

| Properties | Unit | Average Values (from 3 samples) | | |
|---|---|---|---|---|
| | | WAHM-2 | WAHM-3 | WAHM-4 |
| Appearance | | White-Yellow Particles | | |
| Humidity content | % | 11.56 | 10.43 | 11.06 |
| Free Absorbency in salt solution | G/g | 33.8 | 37.9 | 63.5 |
| AUL in salt solution with Areal Polymer Distribution (APD) 0.2 [g/in$^2$] | | | | |
| AUL at 0.3 psi | G/g | 17.4 | 20.5 | 18.4 |
| AUL at 0.6 psi | G/g | 15.3 | 17.9 | 16.5 |
| AUL at 0.9 psi | G/g | 13.8 | 14.5 | 12.3 |
| Relative Gel Rigidity Decreasing after 48 hours (Biodegradation Capacity) | % | 44.6 | 58.3 | 85.7 |

EXAMPLE 5 a) The Chemical Modification of Gelatin

The chemical modification of gelatin is occurred by acylation with phthalic anhydride using the method described by Scholz M. T. (U.S. Pat. No. 4,883,864).

Thus, in a beaker of 5 liter, equipped with stirring rod of anchor type with two blades is prepared 2.8 kg solution of reactant A, by dissolving 280 g of gelatin type A, 175 Bloom, from swine (Aldrich, catalog no. 27, 161-6), with Mv=85,000 (estimated according to the method from Veis A.—"The Macromolecular Chemistry of Gelatin", Academic Press, New York, 1964), $f_{NN2}$=0.65 $10^3$ moles/g and $f_{COOH}$=1.32 $10^{-3}$ moles/g (values estimated after Ward A. C., Courtis A.—"The Science and Technology of Gelatin", Academic Press, New York, 1977) in 1.5 kg water with temperature of 60° C. and a conductivity of 4.3 µS. After dissolving the gelatin is added 1 kg solution of $Na_2CO_3$, with concentration of 9%, and after homogenization of the mixture, in the reaction vessel is added 0.012 kg of phthalic anhydride (Fluka, catalog no. 80020) fresh broke up. The reaction mass is mixed, then, for 6 hours at 40° C. In the end of acylation, the reaction mass is cooled to room temperature and is dialyzed against water with a conductivity of 4.3 µS, for 72 hours, to eliminate the sodium phthalate formed in reaction and the supplementary alkalinity, Periodically is measured the water conductivity in which are immersed the bags for dialysis that contain the phthalylated gelatin (JENWAY Model 4330 conductivity/pH meter—England), is removed the waste water and is replaced by fresh water, and the operations are repeated until after 12 hours of water contact with dialysis bags the conductivity of water remained constant at a value of 4.3 µS.

Further, 1.8 kg chemical modified gelatin solution is used as reactant R1.

b) Synthesis and Processing of Water Absorbing Hybrid Material

In a reaction vessel of 10 Liter, equipped with a stirring rod of anchor type with four blades, thermostatic jacket and thermometer are introduced 7 liter water with a conductivity of 4.3 µS and 2 kg SCRIPSET 520. The aqueous dispersion of reactive polymer B, WD-1, is stirred for 0.5 hours, at room temperature. In the end, the solid phase is separated by filtering at vacuum. The wet solid is washing for 3 times with 2 liter water each time. Is obtained 3.6 kg WS of polymer B. Further, are introduced in a blender of 5 liter, WS of polymer B and 1.4 kg water. The aqueous dispersion resulted, WD-2, is mixed at ambient temperature for 25 minutes, at a speed of 3500 rpm. Is obtained 4.95 kg aqueous dispersion that contain 40% solid phase of reactive polymer B, represents reactant R2.

In a beaker of 5 liter, equipped with stirring rod of anchor type with two blades is prepared 1.4 kg solution of base, by dissolving 0.17 kg NaOH in 1.23 kg water with a conductivity of 4.3 µS. The solution resulted with concentration of 12.1%, represents the reactant R3.

In a dual-shaft jacketed kneader reactor of 20 liter, with a speed ratio between stirrer and shaft $n_1:n_2$ of 1:1.2, with a slow speed of rotor (1) not less than 65 rpm, equipped with a heating-cooling jacket and thermometer are introduced first 4.95 kg reactant R2 and then under mixing is added the whole quantity of 1.8 kg reactant R1. The mixture of reactant R1 and reactant R2 is mixed for 25 minutes, at 40° C. Then is added 1.4 kg reactant R3. The mixing continues 6 hours at 40° C.

Further, the hydrogel mass is profiling with screw extruder, as a bundle of rods with 40 . . . 50 mm in diameter. About 1.5 kg of rods from the quantity of hydrogel was laid on metallic framework covered with screen from polyester with mesh of 100 microns (6 frameworks). These 6 frameworks are introduced in laboratory air circulation oven (Model UT12 FLERAEUS from Kendro Laboratory Products Germany) for drying by water evaporation from wet material. The water evaporation occurred in warm-air current at 60° C., at a speed of air circulation of 1.6 m/s, for 4 hours, controlling from 30 in 30 minutes the humidity content from material.

After drying and cooling at room temperature is obtained 2.32 kg solid material with humidity content of 9.42%. Further, this is grinded with a microfine grinder drive (Model MF10.2 from IKA-WERE GMBH & CO. Germany). Is obtained 2.207 kg of granular material with particles' dimension bigger than 125 microns and smaller than 800 microns and 0.113 kg powder with particles' dimension less than 125 microns.

Further, the granular mass with particles bigger than 125 microns is collected in polyethylene bags and is deposited in conditioning room with air circulation at temperature of 25±5° C. and relative humidity of 45%, for 72 hours.

Finally, is obtained 2.28 kg water absorbent hybrid material (WAHM-5) from which 2.1 kg is packed in polyethylene bags, that after their filling are closed by sealing, and the rest of 0.18 kg WAHM-5 has been putted to the tests that are described in the chapter "Methods of Analysis and Testing".

EXAMPLE 6

The same method of preparing and the same equipment as in Example 5 with the difference that: the reactant R1 is represented by 2.3 kg solution of gelatin type A, 225 Bloom from calf skin (Aldrich, catalog no. 27, 162-4) chemically modified with benzoyl chloride (ACROS, catalog no. 10575); the reactant R3 is represented by 2.4 kg of $NH_4OH$ solution with concentration of 10%; the drying of mass reaction is done at 75° C., for 3 hours, when is obtained a solid material with humidity content of 10.12%. Is obtained 2.68 kg water absorbing hybrid material (WAHM-6)

EXAMPLE 7

The same method of preparing and the same equipment as in Example 5 with the difference that the reactant R2 is prepared using poly(styrene-alt-maleic anhydride) with Mn=50,000 (ACROS catalog no. 7925-2500) as an aqueous dispersion of polymer B and the intercoupling reaction occurs at 55° C. for 8 hours. It is obtained 2.18 kg water absorbing hybrid material (WAHM-7). The properties of WAHM obtained from the experiments 5-7 are presented in table 3.

$f_{NN2}=0.65 \cdot 10^{-3}$ moles/g and $f_{COOH}=1.32 \cdot 10^{-3}$ moles/g (values estimated according to Ward A. C., Courtis A.—"The Science and Technology of Gelatin", Academic Press, New York, 1977) in 1.35 kg water with temperature of 50° C. and conductivity of 4.3 µS. The solution had a concentration of 10%, represents the reactant R1.

In a reaction vessel of 10 liter, equipped with a stirring rod of anchor type with four blades, thermostatic jacket and thermometer are introduced 7 liter water with a conductivity of 4.3 µS and 2.5 kg SCRIPSET 520 (poly(styrene-co-maleic anhydride)) with an average molecular mass of 350,000 Da from Hercules Incorporated as reactant B, with a functionality in anhydride groups $f_r^B=0.00286$ moles of maleic anhydride per 1 g polymer, evaluated by the method which is based on reaction of anhydride groups with morpholine and titration of morpholine in excess with perchloric acid in acetic acid (Okay O., "Porous Maleic Anhydride-Styrene-Divinylbenzene Copolymer Beads", *J. Appl. Plym. Sci.*, 34, 307-317, 1987). Aqueous dispersion of reactive polymer B, W-1, is stirred 0.5 hours at room temperature and the solid phase is separated by filtration at vacuum. The wet solid is washed of 3 times with 2 liter water each time. It is obtained 6.2 kg wet solid (WS) of polymer B. Further, is introduced in a blender of 5 liter, WS of polymer B and 1.3 kg water. The aqueous dispersion WD-2 is mixed at room temperature for 15 minutes, at a speed of 3500 rpm. Is resulted 7.5 kg aqueous dispersion, which contain 25% solid phase of reactive polymer B, represents the reactive R2.

TABLE 3

Technical characteristics for WAHM-5; WAHM-6 and WAHM-7

| Properties | Unit | Average Values (from 3 samples) | | |
|---|---|---|---|---|
| | | WAHM-5 | WAHM-6 | WAHM-7 |
| Appearance | | White-Yellow Particles | | |
| Humidity content | % | 10.63 | 9.74 | 11.88 |
| Free Absorbency in water | G/g | 164.7 | 138.5 | 181.2 |
| Free Absorbency in salt solution | G/g | 40.2 | 42.6 | 51.7 |
| AUL in salt solution with Areal Polymer Distribution (APD) 0.2 [g/in²] | | | | |
| AUL at 0.3 psi | G/g | 18.9 | 19.3 | 16.4 |
| AUL at 0.6 psi | G/g | 16.4 | 17.1 | 14.6 |
| AUL at 0.9 psi | G/g | 14.3 | 15.6 | 12.8 |
| Free Absorbency in baby milk | G/g | 53.6 | 46.8 | 54.6 |
| AUL in baby milk with Areal Polymer Distribution (APD) 0.1 [g/in²] at 0.1 psi | G/g | 42.3 | 39.7 | 23.6 |
| Centrifuge Retention Capacity (CRC)in salt solution | G/g | 21.3 | 22.2 | 18.7 |
| pH 1 g in 100 ml salt solution | | 6.05 | 6.83 | 6.44 |
| Gel Rigidity, in salt solution | KPa | 1.14 | 2.06 | 0.97 |
| Relative Gel Rigidity Decreasing after 48 hours (Biodegradation Capacity) | % | 55.9 | 73.8 | 24.9 |

EXAMPLE 8

In a 5 liter beaker, equipped with stirring rod of anchor type with two blades is prepared 1.5 kg solution of reactant A, by dissolving 150 g of gelatin type A, 175 Bloom, from swine (Aldrich, catalog no. 27, 161-6), with Mv=85,000 (estimated according to the method from Veis A.—"The Macromolecular Chemistry of Gelatin", Academic Press, New York, 1964), In a 5 liter beaker, equipped with stirring rod of anchor type with two blades is prepared 2.8 kg solution of base, by dissolving 1000 grams solution of $NH_3$ of concentration 28% (Aldrich, catalog no. 38,053-9) in 1.8 kg water with a conductivity of 4.3 µS. The resulted solution represents the reactant R3.

In a dual-shaft jacketed kneader reactor of 20 liter, with a speed ratio between stirrer and shaft $n_1:n_2$ of 1:1.2 with a slow speed of rotor (1) not less than 60 rpm, equipped with a heating-cooling jacket and thermometer are introduced first 7.5 kg reactant R2 and then under mixing is added the whole quantity of 1.5 kg reactant R1. The mixture of reactant R1 and reactant R2 is mixed for 15 minutes, at temperature of 35° C.

Then is added 2.8 kg reactant R3. The mixing continues for 3 hours at 35° C.

After evacuation of reaction mass from kneader, is obtained 11.8 kg of transparent granular hydrogel, very elastic.

Further, the hydrogel mass is profiling with screw extruder, having the same constructive characteristics with device called "meat chopper", as a bundle of rods with 90 ... 100 mm in diameter. About 1.5 kg of rods from the quantity of hydrogel was lay on metallic framework covered with screen from polyester with mesh of 100 microns (6 frameworks). These 6 frameworks are introduced in laboratory air circulation oven (Model UT12 HERAEUS from Kendro Laboratory Products Germany) for drying by water evaporation from wet material. The water evaporation occurred in warm-air current at 75° C., at a speed of air circulation of 1 m/s for 3.5 hours, controlling from 30 in 30 minutes the humidity content from material, by gravimetrical method, with Moisture analyzer (Model SMO 01 from BOECO GERMANY).

After drying and cooling at room temperature is obtained 3.18 kg of solid material with humidity content of 7.86%. Further, this is grinded with a microfine grinder drive (Model MF10.2 from IKA-WERKE GMBH & CO. Germany). Is obtained 3.02 kg of granular material with particles' dimension bigger than 250 microns and smaller than 2500 microns and 0.16 kg of powder with particles' dimension less than 250 microns (the grading analysis has been done with Vibratory Sieve Shaker "Analysette 3" equipped with a control and evaluation programme "AUTOSIEVE for Windows" from FRITSCH GMBH Germany).

Further, the granular mass with particles bigger than 250 microns is collected in polyethylene bags and is deposited in conditioning room with air circulation at temperature of 25±5° C. and relative humidity of 65%, for 48 hours.

Finally, is obtained 3.03 kg water absorbent hybrid material (WAHM-1) from which 2.8 kg is packed in polyethylene bags, that after their filling are closed by sealing, and the rest of 0.23 kg WAHM-1 has been putted to the tests that are described in the chapter "Methods of Analysis and Testing".

The properties of WAHM-8 are presented in table 4.

Figure 4:
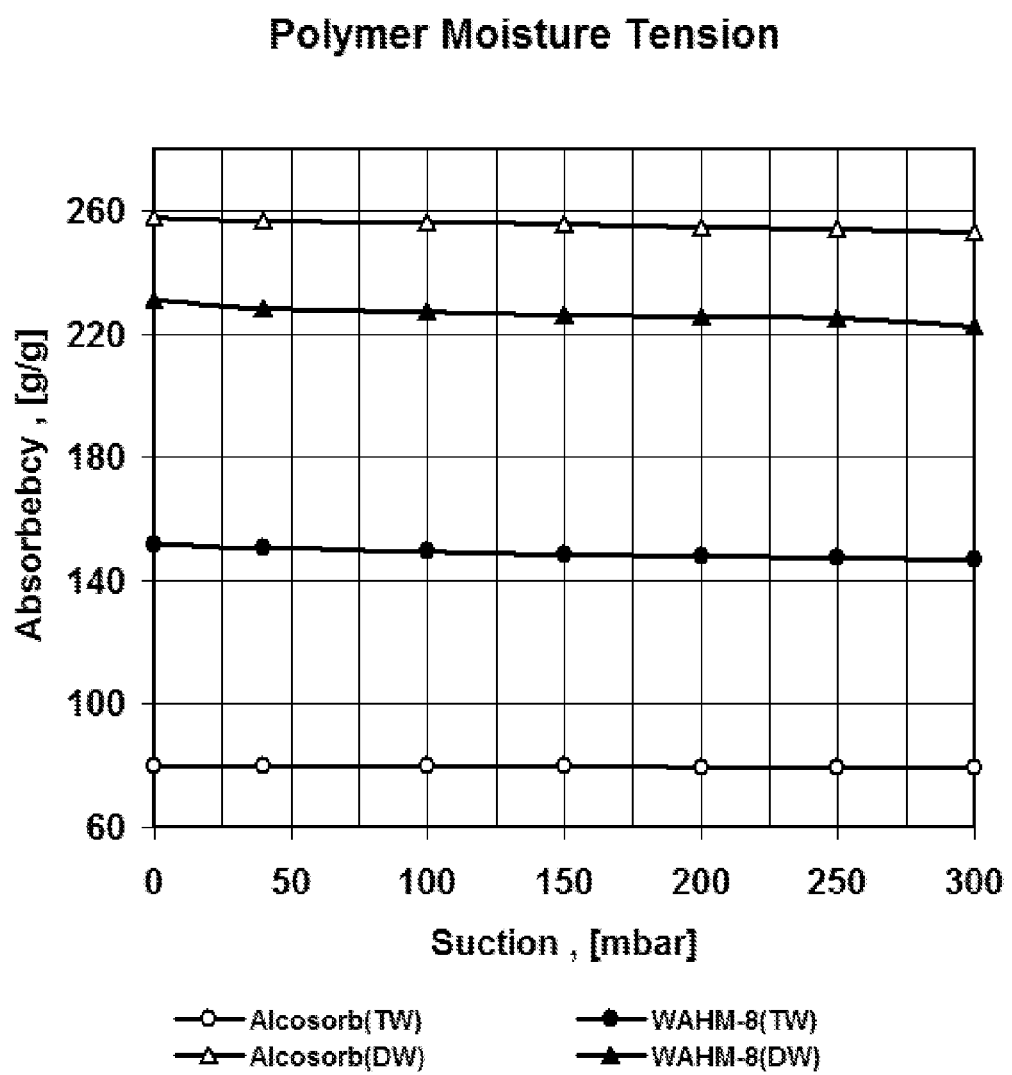
FIG. 4. Absorbency (gig) versus suction (mbar) for WAHM-8 and ALCOSORB 400 in distillate water (DW) and tap water (TW)

Polymer moisture tension of WAHM-8 and ALCOSORB 400 evaluated in conformity with the method "polymer moisture tension" from the chapter "Methods of Analysis and Testing" is presented in FIG. 4.

U.S. Patent Documents

The Contents of the Following Documents are Incorporated Herein by Reference:

| | | |
|---|---|---|
| RE33,997 | Jul. 14, 1992 | Kuzma, et al. |
| 6,444,653 | Sep. 3, 2002 | Serge, et al. |
| 6,107,432 | Aug. 22, 2000 | Engelhardt, et al. |
| 6,071,447 | Jun. 6, 2000 | Bootman, et al. |
| 5,945,101 | Aug. 31, 1999 | Berg, et al. |
| 5,847,089 | Dec. 8, 1998 | Damodaran, et al. |
| 5,847,031 | Dec. 8, 1998 | Klimmek, et al. |
| 5,847,013 | Dec. 8, 1998 | Ross, et al. |
| 5,736,595 | Apr. 7, 1998 | Gunther, et al. |
| 5,733,994 | Mar. 31, 1998 | Koepff, et al. |
| 5,712,316 | Jan. 27, 1998 | Dahmen, et al. |
| 5,629,377 | May 13, 1997 | Burgert, et al. |
| 5,567,478 | Oct. 22, 1996 | Houben, et al. |
| 5,565,519 | Oct. 15, 1996 | Rhee, et al. |
| 5,549,914 | Aug. 27, 1996 | Farber |
| 5,487,895 | Jan. 30, 1996 | Dapper, et al. |
| 5,453,323 | Sep. 26, 1995 | Chambers, et al. |
| 5,408,019 | Apr. 18, 1995 | Mertens, et al. |
| 5,376,375 | Dec. 27, 1994 | Rhee, et al. |
| 5,292,802 | Mar. 8, 1994 | Rhee, et al. |
| 5,284,936 | Feb. 8, 1994 | Donachy, et al. |
| 5,190,533 | Mar. 2, 1993 | Blackburn |
| 5,118,719 | Jun. 2, 1992 | Lind |
| 4,959,341 | Sep. 25, 1990 | Wallach |
| 4,952,550 | Aug. 28, 1990 | Wallach, et al. |
| 4,944,734 | Jul. 31, 1990 | Wallach |
| 4,883,864 | Nov. 28, 1989 | Scholz |
| 4,855,179 | Aug. 8, 1989 | Bourland, et al. |
| 4,833,222 | May 23, 1989 | Siddall, et al. |
| 4,808,637 | Feb. 28, 1989 | Boardman, et al. |
| 4,666,983 | May 19, 1987 | Tsubakimoto, et al. |
| 4,654,039 | Mar. 31, 1987 | Brandt, et al. |
| 4,610,678 | Sep. 9, 1986 | Weisman, et al. |
| 4,525,527 | Jun. 25, 1985 | Takeda, et al. |
| 4,416,814 | Nov. 22, 1983 | Battista |
| 4,389,513 | Jun. 21, 1983 | Miyazaki |
| 4,349,470 | Sep. 14, 1982 | Battista |
| 4,264,493 | Apr. 28, 1981 | Battista |
| 4,190,562 | Feb. 26, 1980 | Westerman |
| 4,124,748 | Nov. 7, 1978 | Fujimoto, et al. |
| 4,117,184 | Sep. 26, 1978 | Erickson, et al. |
| 4,090,013 | May 16, 1978 | Ganslaw et al. |
| 4,076,663 | Feb. 28, 1978 | Masuda, et al. |
| 3,997,484 | Dec. 14, 1976 | Weaver, et al. |

TABLE 4

Technical characteristics for WAHM-8 and commercial product ALCOSORB 400

| Properties | Unit | WAHM-8 Average Values (from 3 samples) | ALCOSORB400 Average Values (from 3 samples) |
|---|---|---|---|
| Appearance | | White-Yellow Particles | White particles |
| Humidity content | % | 7.83 | 8.15 |
| Free Absorbency in distillate water | G/g | 231 | 258 |
| Free Absorbency in tap water | G/g | 152 | 80 |
| AUL in distillate water with Areal Polymer Distribution (APD) 0.2 [g/in$^2$], at 0.3 psi | G/g | 52.11 | 16.59 |
| AUL in tap water with Areal Polymer Distribution (APD) 0.2 [g/in$^2$], at 0.3 psi | G/g | 33.69 | 15.61 |
| Relative Gel Rigidity Decreasing after 1 week (Biodegradation Capacity) | % | 98.36 | 100 |

-continued

| 3,983,095 | Sep. 28, 1976 | Bashaw, et al. |
| 3,980,663 | Sep. 14, 1976 | Gross |
| 3,959,569 | May 25, 1976 | Burkholder, Jr. |
| 3,935,099 | Jan. 27, 1976 | Weaver, et al. |
| 3,926,891 | Dec. 16, 1975 | Gross et al. |
| 3,926,869 | Dec. 16, 1975 | Horle et al. |
| 3,224,986 | Dec. 21, 1965 | Butler et al. |

OTHER REFERENCES

The contents of the following documents are incorporated herein by reference:

Bucholz F. L., Graham A. T., "Modern Superabsorbent Polymer Technology", John Wiley & Sons Inc. 1998
Bo J., "Study on PVA Hydrogel Crosslinked by Epichlorohydrin", J. Appl. Polym. Sci., 46, 783-786, 1992
Fernandez-Nieves J. A., Fernandez-Barbero, Vincent B., Nieves F. J., "Charge Controlled Swelling of Microgel Particles", Macromolecules, 33, 2114-2118, 2000
Foster L. J. R., Fuller R. C., Lenz R. W.—in "Hydrogels and Biodegradable Polymers for Bioapplications", Ottenbrite R. M., Huang S. J., Park K. (Editors), ACS Symposium Series 627, American Chemical Society, Washington, D.C. 1996
Amass W., Amass A., Tigle B.—"A Review of Biodegradable Polymers: Uses, Current Developments in the Synthesis and Characterization of Biodegradable Polyesters, Blends of Biodegradable Polymers and Recent Advances in Biodegradation Studies", *Polymer International* 47, 89, 1998
Volke-Sepulveda T., Favela-Torres E., Manzur-Guzman A., Limon-Gonzalez M., Trejo-Quintero G.—"Microbial Degradation of Thermo-Oxidized Low-Density Polyethylene" *J. Appl. Polym. Sci.*, 73, (1999), 1435
Reeve M. S., McCarthy S. P., Downey M. J., Gross R. A.—"Polylactide Stereochemistry: Effect on Enzymatic Degradability" *Macromolecules*, 27, (1994), 825
Wool R. P., Raghavan D., Wagner G. C., Billieux S.—"Biodegradation Dynamics of Polymer-StarchComposites", J. Appl. Polym. Sci., 77, (2000), 1643
Thakore I. M., Iyer S., Desai A., Lele A., Devi S. "Morphology, Thermomechanical Properties, and Biodegradability of Low Density Polyethylene/Starch Blends" *J. Appl. Polum. Sci.*, 74, (1999), 2791
Perrone C.—"Biodegradabilita delle Materie Plastiche", *Poliplasti* 398/399—january/february 1991, p. 66
Black J., "Biological Performance of Materials: Fundamentals of Biocompatibility", 2d ed. M. Dekker, N.Y., 1992).
Hoffman A. S., Daly C. H., "Biology of Collagen", Viidik Vunst J. Eds., Academic Press, New York, 1980
Ward A. G., Courts A., "The Science and Technology of Gelatin", Academic Press N.Y., 1977
Veis A.—"The Macromolecular Chemistry of Gelatin", Academic Press, New York, 1964
Okay O., "Porous Maleic Anhydride-Styrene-Divinylbenzene Copolymer Beads", *J. Appl. Plym. Sci.,* 34,307-317, 1987
Nijenhuis K., "Thermoreversible Networks-Viscoelastic Properties and Structure of Gels", *Advances in Polymer Science,* 130, 1-252, 1997
Klempner D., Frisch K. C.—"Advances in Interpenetrating Polymer Networks", vol I Technomic. Publ. Co. Inc. Lancaster, SUA, 1990

We claim:

1. A process for preparing a biocompatible, biodegradable, macromolecular water-absorbent hybrid material, having a three-dimensional configuration with intermolecular covalent bonds and containing free functional groups selected from OH, SH, $NH_2$ and COOH, said polymer being formed by polymer-polymer intercoupling reaction between a natural water-soluble polymer A or a derivative thereof having a molecular weight between 20,000 and 300,000Da, and a synthetic polymer B in a ratio of A to B between 1 and 50% of the dry mixture (A+B), wherein the natural polymer A is selected from:

amphoteric reactants, partially denatured or chemically modified natural polymers, that dissociate in water to form both anions and cations, and which can undergo polymer-polymer intercoupling reactions, and wherein:

synthetic polymer B is a linear or branched reactive synthetic copolymer having a molecular weight of 50,000-500,000Da derived from a vinyl monomer and an ethylenically unsaturated monomer, said copolymer having a backbone with polymeric subunits $R_n$ and $R_r$, wherein R represents a subunit covalently bonded to the polymer backbone, n represents nonreactive chemical functional groups and r represents reactive chemical functional groups said method comprising reacting a solution of the natural polymer A in water with a suspension of the synthetic polymer B in water in the absence of a cross linking or coupling agent, thereby forming the biocompatible, biodegradable, macromolecular water-absorbent hybrid material.

2. A method for preparing a biocompatible, biodegradable, macromolecular water absorbent hybrid material having a three-dimensional configuration with intermolecular covalent bonds and containing free functional groups selected from the group consisting of —OH, —SH, —$NH_2$ and —COOH, comprising reacting an aqueous solution of a natural water-soluble polymer A with an aqueous suspension of a synthetic polymer B to form a water-absorbent hybrid material by a polymer-polymer intercoupling reaction.

3. Method according to claim 2, wherein said polymer-polymer intercoupling reaction is conducted at a temperature in the range of 35-55 degrees Celsius.

4. The method of claim 2, further comprising washing said synthetic polymer B with water prior to reacting said synthetic polymer B with said natural water-soluble polymer A.

5. The method of claim 2 wherein the natural polymer is collagen, a collagenic biopolymer, gelatin, gelatin modified by reaction with an anhydride or acid chloride, alfa-keratose, gamma-keratose, keratin hydrolysate, elastin, fibrin, casein, or soybean protein.

6. The method of claim 5, wherein the natural polymer is gelatin.

7. The method of claim 6, wherein the synthetic polymer is poly(styrene-co-maleic anhydride).

8. Method according to claim 2, wherein said natural water-soluble polymer A is a protein modified by reaction with an anhydride or acid chloride.

9. The method of claim 2, wherein the synthetic polymer B is poly (ethylene-alt-maleic anhydride), poly (ethylene-graft-maleic anhydride), poly (isobutylene-co-maleic anhydride), poly(isoprenegraft-maleic anhydride), poly (maleic anhydride-co-1-octadecene), polypropylene-graft-maleic anhydride), or poly (styrene-co-maleic anhydride).

10. The method of claim 2, wherein the natural polymer has at least $1\times10^{-3}$ moles —COOH/g and at least $0.5\times10^{-3}$ moles —$NH_2$/g, and said natural polymer has an isoelectric point of not less than 2.5 and not more than 10.5.

11. The method of claim 2, wherein the ionic reactive chemical functionality of polymer B is not less than $5\times10^{-3}$ moles "r"/g and not more than $1\times10^{-2}$ moles "r"/g.

12. The method of claim 2, wherein said polymer-polymer intercoupling reaction is conducted in the presence of a base.

13. The method of claim 12, wherein said base is NaOH, $NH_3$, or LiOH.

14. The process of claim 1, wherein the natural polymer forms in water $COO^-$ anions and $NH_3^\pm$ cations with at least $1\times10^{-3}$ moles COOH/g and at least $0.5\times10^{-3}$ moles $NH_2$/g with an isoelectric point not less than 2.5 and not more than 10.5.

15. The method of claim 2, wherein the natural polymer is selected from the group consisting of collagen, atelocollagen, solubilized collagen, gelatin, collagen hydrolysate, alpha-keratose, gamma-keratose, keratin hydrolysate, elastin and derivatives, fibrin, fibroin, ovalbumin, bovine serum albumin, casein, soybean protein and derivatives of any of the foregoing polymers.

16. The method of claim 2, wherein the natural polymer is gelatin.

17. The method of claim 2, wherein the natural polymer is chemically modified by acylation reaction using a modifying agent selected from anhydrides and acid chlorides.

18. The method of claim 17, wherein the modifying agent is selected from the group consisting of phthalic anhydride, maleic anhydride, citraconic anhydride, itaconic anhydride, succinic anhydride, benzoyl chloride, benzenesulfonyl choride and butyryl chloride.

19. The method of claim 1, wherein R includes a spacer group interposed between the chemical function and the chain that is anchored to it.

20. The method of claim 19, wherein the spacer group is selected from —CO—O— and —$(CH_2)_n$— where n equals 1-4.

21. The method of claim 1, wherein the reactive chemical functions of synthetic polymer B, are chemical functions $R_r$, selected from —CO—O—CO— and —CO—NHCO—.

22. The method of claim 21, wherein the reactive chemical function is selected from maleic anhydride, itaconic anhydride, citraconic anhydride, 2-octenylsuccinic anhydride and corresponding imides.

23. The method of claim 1, wherein the ionic reactive chemical functionality of polymer B, is symbolized as $f_r^B$, and is not less than $5\times10^{-3}$ moles "r"/g and not more than $1\times10^{-2}$ moles "r"/g.

24. The method of claim 1, wherein the non-reactive chemical functions $R_n$ can comprise 1 to 4 groups selected from hydrogen, aliphatic or aromatic hydrocarbon residues with 1 to 20 carbon atoms, non-active ester, ether, or imino groups and nonactive halogen derivatives.

25. The method of claim 1, wherein the synthetic polymer B is prepared from monomers comprising monomers with non-reactive groups, selected from the group consisting of styrene, alpha-methyl styrene, alkylated styrenes, vinyl-toluene, vinyl esters of saturated $C_1$-$C_4$-carboxylic acids, alkyl vinyl ethers with at least 2 carbon atoms in the alkyl group, acrylate esters, methacrylate esters; conjugated diolefins; allenes;

olefin halides, ethylene, propene, isobutylene, butadiene, isoprene, esters of monoethylenically unsaturated $C_3$-$C_6$-carboxylic acids, N-vinyllactams, acrylic and methacrylic esters of alkoxylated monohydric saturated alcohols, vinyl pyridine and vinyl morpholine, N-vinyl-formamide, dialkyldiallylammonium halides, N-vinylimidazoles, N-vinylimidazolines, acrylamide, methacrylamide and acrylonitrile.

26. The method of claim 25, wherein the monomers with non-reactive groups are selected from the group consisting of ethylene, propene, styrene, isobutylene, vinyl acetate, methyl acrylate, methyl methacrylate, acrylamide, vinylether, N-vinylpyrrolidone, acrylic acid, methacrylic acid and maleic acid.

27. The method of claim 25, wherein the synthetic polymer B is selected from poly (ethylene-alt-maleic anhydride), poly (ethylene-graft-maleic anhydride), poly(isobutylene-co-maleic anhydride), poly(isoprene-graft-maleic anhydride), poly (maleic anhydride-co-1-octadecene), polypropylene-graft-maleic anhydride), and poly(styrene-co-maleic anhydride).

* * * * *